United States Patent [19]
Willner et al.

[11] Patent Number: 5,622,929
[45] Date of Patent: Apr. 22, 1997

[54] THIOETHER CONJUGATES

[75] Inventors: David Willner, Hamden; Pamela A. Trail, Farmington; H. Dalton King, Hamden; Sandra J. Hofstead, Middletown; Robert S. Greenfield, Wallingford; Gary R. Braslawsky, Glastonbury, all of Conn.

[73] Assignee: Bristol-Myers Squibb Company, New York, N.Y.

[21] Appl. No.: 824,951

[22] Filed: Jan. 23, 1992

[51] Int. Cl.$^6$ .......................... A61K 38/16; A61K 31/70; C07K 9/00; C07H 15/24
[52] U.S. Cl. ................ 514/8; 514/34; 530/322; 536/6.4
[58] Field of Search .................. 514/34, 249.8; 536/6.4, 22, 17.4, 17.6; 530/387.2, 322; 548/422; 540/478

[56] References Cited

U.S. PATENT DOCUMENTS

| | | | |
|---|---|---|---|
| 5,002,883 | 3/1991 | Bieniarz et al. | 435/176 |
| 5,024,834 | 6/1991 | Houston et al. | 424/85.91 |
| 5,055,561 | 10/1991 | Packard et al. | 530/390 |
| 5,066,490 | 11/1991 | Neville et al. | 424/85.91 |

FOREIGN PATENT DOCUMENTS

| | | |
|---|---|---|
| 0328147 | 8/1989 | European Pat. Off. . |
| 0457250 | 11/1991 | European Pat. Off. . |
| WO91/13356 | 9/1991 | WIPO . |

*Primary Examiner*—Elli Peselev
*Attorney, Agent, or Firm*—Bristol-Myers Squibb Co.

[57] ABSTRACT

Provided are drug/ligand compounds of Formula (I):

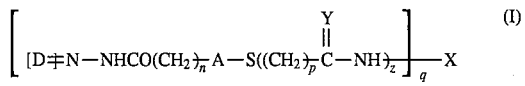

in which
D is a drug moiety;
n is an integer from 1 to 10;
p is an integer from 1 to 6;
Y is O or $NH_2{}^+Cl^-$;
z is 0 or 1;
q is about 1 to about 10;
X is a ligand; and,
A is a Michael Addition Adduct.

In a preferred embodiment, the ligand is an immunoglobulin, preferably a chimeric antibody or fragment thereof. Also provided are formulations comprising as an active ingredient a compound of Formula (I), intermediates useful for preparing the compounds of Formula (I), processes for preparing the compounds of Formula (I), and methods for using the compounds of the invention.

52 Claims, 17 Drawing Sheets

THIOETHER CONJUGATES

SUMMARY OF THE INVENTION

Bifunctional compounds which link cytotoxic reagents to antibodies are known. These compounds have been particularly useful in the formation of immunoconjugates directed against tumor associated antigens. Such immunoconjugates allow the selective delivery of toxic drugs to tumor cells. (See e.g., Hermentin and Seiler, "Investigations With Monoclonal Antibody Drug Conjugates," *Behring Insti. Mitl.* 82:197–215 (1988); Gallego et al., "Preparation of Four Daunomycin-Monoclonal Antibody 791T/36 Conjugates With Anti-Tumor Activity". *Int. J. Cancer* 33:737–44 (1984); Arnon et al., "In Vitro and In Vivo Efficacy of Conjugates of Daunomycin With Anti-Tumor Antibodies," *Immunological Rev.* 62:5–27 (1982)

Greenfield et al. have recently described the formation of acid-sensitive immunoconjugates containing the acylhydrazine compound, 3-(2-pyridyldithio)propionyl hydrazide conjugated via an acylhydrazone bond to the 13-keto position of an anthracycline molecule, and conjugation of this anthracycline derivative to an antibody molecule (Greenfield et al., European Patent Publication EP 0 328 147, published Aug. 16, 1989, which corresponds to pending U.S. Ser. No. 07/270,509, filed Nov. 16, 1988 and U.S. Ser. No. 07/155,181, filed Feb. 11, 1988, now abandoned). This latter reference also discloses specific thioether-containing linkers and conjugates, including hydrazone thioether containing immunoconjugates. Kaneko et al. (U.S. Ser. No. 07/522,996, filed May 14, 1990, which is equivalent to European Patent Publication, EP A 0 457 250, published Nov. 21, 1991) have also described the formation of conjugates containing anthracycline antibiotics attached to a bifunctional linker by an acylhydrazone bond at the C-13 position of an anthracycline molecule. In their invention the linkers contain a reactive pyridinyldithio- or an ortho-nitrophenyldithio- group, by which the linker reacts with a suitable group attached to a cell reactive ligand, to form the completed conjugate.

It would be useful to provide additional compounds which contain an acid-sensitive linkage between the targeting and reagent molecules for use in therapy in vivo. Thus, the present invention provides a novel chemistry for linking a therapeutically active drug molecule to a ligand capable of recognizing a selected target cell population. This linker chemistry then is used to prepare therapeutically active conjugates. Also provided by the invention are formulations containing the conjugates, a process for preparing a conjugate of the invention, a method for treating or preventing a selected disease state which comprises admininistering to a patient a conjugate of the invention and a novel method for preparing a reduced antibody which is useful as a targeting ligand for use in preparing a conjugate of the invention.

According to the invention each drug molecule is linked to the ligand via a thioether-containing linker arm. The drug is attached to that linker through an acylhydrazone bond. The thioether bond is created by reaction of a sulfhydryl group on the ligand, or on a short "spacer" moiety attached to the ligand, with a "Michael Addition Receptor" which becomes, after the reaction, a "Michael Addition Adduct". In a preferred embodiment, the targeting ligand is attached directly to the linker through a covalent thioether bond.

The novel conjugate so formed has the general structure of Formula (I):

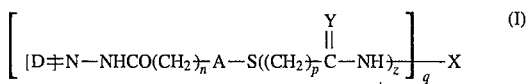

in which

D is a drug moiety;

n is 1 to 10;

p is 1 to 6;

Y is O or $NH_2^+Cl^-$;

z is 0 or 1;

q is about 1 to about 10;

X is a ligand; and,

A is Michael Addition Adduct moiety.

In a one embodiment the drug moiety is an anthracycline antibiotic and the ligand is an antibody.

In a preferred embodiment the anthracycline is bound to the linker portion of the conjugate through an acylhydrazone bond at the 13-keto position of the anthracycline compound. The antibody then is bound, through the linker, to the anthracycline compound. In an especially preferred embodiment, this linkage occurs through a reduced disulfide group (i.e. a free sulfhydryl group (—SH)) on an antibody).

In a most preferred embodiment the anthracycline drug moiety is adriamycin, the Michael Addition Receptor, from which the Michael Addition Adduct is derived, is a maleimido-group, and the antibody moiety is a chimeric antibody.

The conjugates of the invention retain both specificity and therapeutic drug activity for the treatment of a selected target cell population. They may be used in a pharmaceutical composition, such as one comprising a pharmaceutically effective amount of a compound of Formula (I) associated with a pharmaceutically acceptable carrier, diluent or excipient.

BRIEF DESCRIPTION OF THE DRAWINGS

FIG. 1(*b*) provides a synthetic scheme for preparing an immunoconjugate of the invention in which the ligand is a SPDP-thiolated antibody.

FIG. 1(*c*) provides a synthetic scheme for preparing an immunoconjugate of the invention in which the ligand is an iminothiolane-thiolated antibody.

DETAILED DESCRIPTION OF THE INVENTION

Figure 1A:
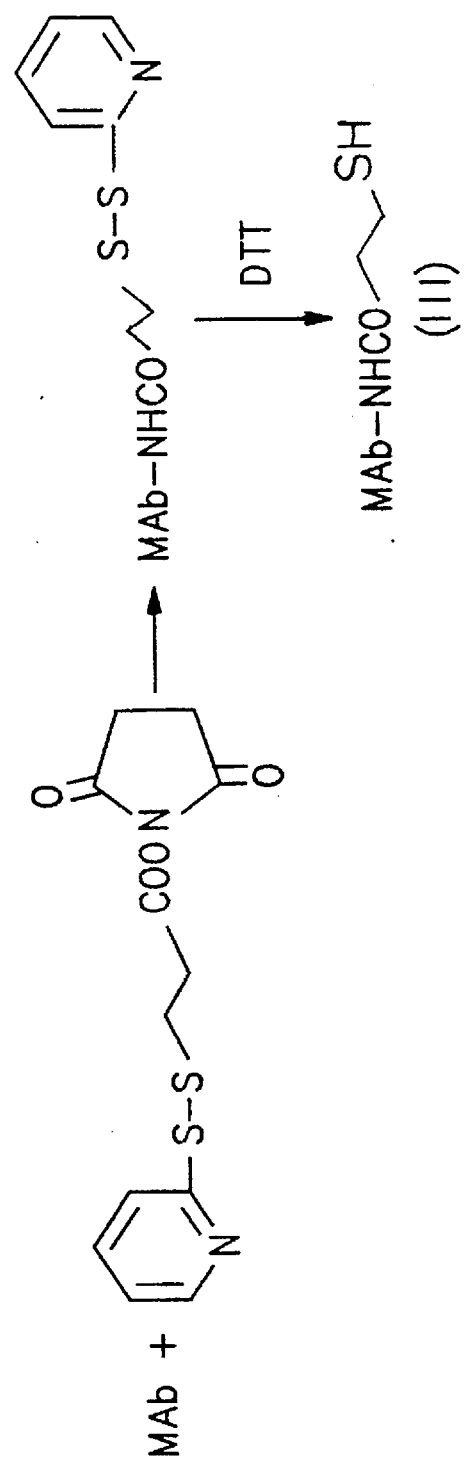
FIG. 1(*a*) provides a synthetic scheme for preparing a thiolated antibody using SPDP as the thiolation agent.

The following detailed description is provided so that the invention may be more fully understood.

The present invention provides novel drug conjugates composed of a ligand capable of targeting a selected cell population, a drug, and a thioether-containing linker which joins the ligand and the drug. The drug is joined to the linker through an acylhydrazone bond. In a preferred embodiment, the ligand is joined directly to the linker through a thioether bond. Normally, this bond will be created by reaction of a reactive sulfhydryl (—SH) group on the ligand, or on a spacer moiety (e.g., one derived from the SPDP or iminothiolane chemistry described below), with a Michael Addition Receptor.

The invention also provides methods for the production of these drug conjugates and pharmaceutical compositions and methods for delivering the conjugates to target cells in which a modification in biological process is desired, such as in the treatment of diseases such as cancer, viral or other pathogenic infections, autoimmune disorders, or other disease states.

The conjugates comprise at least one drug molecule connected by a linker of the invention to a targeting ligand molecule that is reactive with the desired target cell population. The ligand molecule can be an immunoreactive protein such as an antibody, or fragment thereof, a non-immunoreactive protein or peptide ligand such as bombesin or, a binding ligand recognizing a cell associated receptor such as a lectin or steroid molecule.

As previously noted, a conjugate of the invention is represented by general Formula (I):

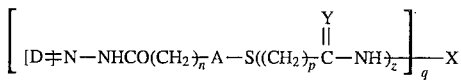

(I)

in which

D is a drug molecule;

n is 1 to 10;

p is 1 to 6;

Y is O or $NH_2^+Cl^-$;

z is 0 or 1;

q is about 1 to about 10;

X is a ligand; and,

A is Michael Addition Adduct

For a better understanding of the invention, the drugs and ligands will be discussed individually. The intermediates used for the preparation of the conjugates and the synthesis of the conjugates then will be explained.

THE DRUG

One skilled in the art understands that the present invention requires the drug and ligand to be linked by means of an acylhydrazone linkage, through a Michael Addition Adduct and thioether-containing linker. Neither the specific drug nor the specific ligand is to be construed as a limitation on the present invention. The linkers of the present invention may be used with any drug having any desired therapeutic, biological activity-modifying or prophylactic purpose, limited only in that the drug used in preparing the conjugate be able to form an hydrazone bond. Preferably, to prepare the hydrazone, the drug should have a reactively available carbonyl group, such as, for example, a reactive aldehyde or ketone moiety (represented herein as "[D-(C=O)]") which is capable of forming a hydrazone (i.e. a —C=N—NH— linkage). The drug hydrazone linkage is represented herein as "[D=N—NH—". In addition, the reaction of that reactively available group with the linker preferably must not destroy the ultimate therapeutic activity of the conjugate, whether that activity is the result of the drug being released at the desired site of action or whether the intact conjugate, itself, is responsible for such activity.

One skilled in the art understands that for those drugs which lack a reactively available carbonyl group, a derivative containing such a carbonyl group may be prepared using procedures known in the art. As can be appreciated, the conjugate prepared from such derivatized drug must retain therapeutic activity when present at the active site, whether this is due to the intact conjugate, or otherwise. Alternatively, the derivatized drug or, for example, a prodrug, must be released in such a form that a therapeutically active form of the drug is present at the active site.

The present linker invention may be used in connection with drugs of substantially all therapeutic classes including, for example, antibacterials, anti-virals, antifungals, anticancer drugs, antimycoplasmals, and the like. The drug conjugates so constructed are effective for the usual purposes for which the corresponding drugs are effective, and have superior efficacy because of the ability, inherent in the ligand, to transport the drug to the desired cell where it is of particular benefit.

Further, because the conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, α-interferon, β-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

The preferred drugs for use in the present invention are cytotoxic drugs, particularly those which are used for cancer therapy. Such drugs include, in general, alkylating agents, anti-proliferative agents, tubulin binding agents and the like. Preferred classes of cytotoxic agents include, for example, the anthracycline family of drugs, the vinca drugs, the mitomycins, the bleomycins, the cytotoxic nucleosides, the pteridine family of drugs, diynenes, and the podophyllotoxins. Particularly useful members of those classes include, for example, adriamycin, carminomycin, daunorubicin, aminopterin, methotrexate, methopterin, dichloromethotrexate, mitomycin C, porfiromycin, 5-fluorouracil, 6-mercaptopurine, cytosine arabinoside, podophyllotoxin, or podophyllotoxin derivatives such as etoposide or etoposide phosphate, melphalan, vinblastine, vincristine, leurosidine, vindesine, leurosine and the like. As noted previously, one skilled in the art may make chemical modifications to the desired compound in order to make reactions of that compound more convenient for purposes of preparing conjugates of the invention.

A highly preferred group of cytotoxic agents for use as drugs in the present invention include drugs of the following formulae:

THE METHOTREXATE GROUP OF FORMULA (2):

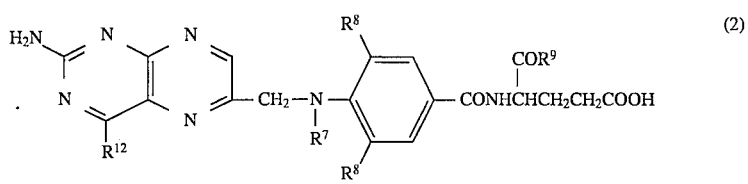

(2)

in which $R^{12}$ is amino or hydroxy;
$R^7$ is hydrogen or methyl;
$R^8$ is hydrogen, fluoro, chloro, bromo or iodo;
$R^9$ is hydroxy or a moiety which completes a salt of the carboxylic acid;

THE MITOMYCIN GROUP OF FORMULA (3):

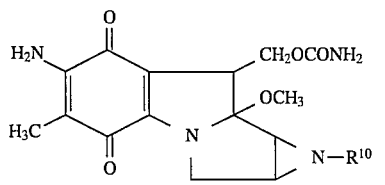

(3)

in which $R^{10}$ is hydrogen or methyl;

THE BLEOMYCIN GROUP OF FORMULA (4):

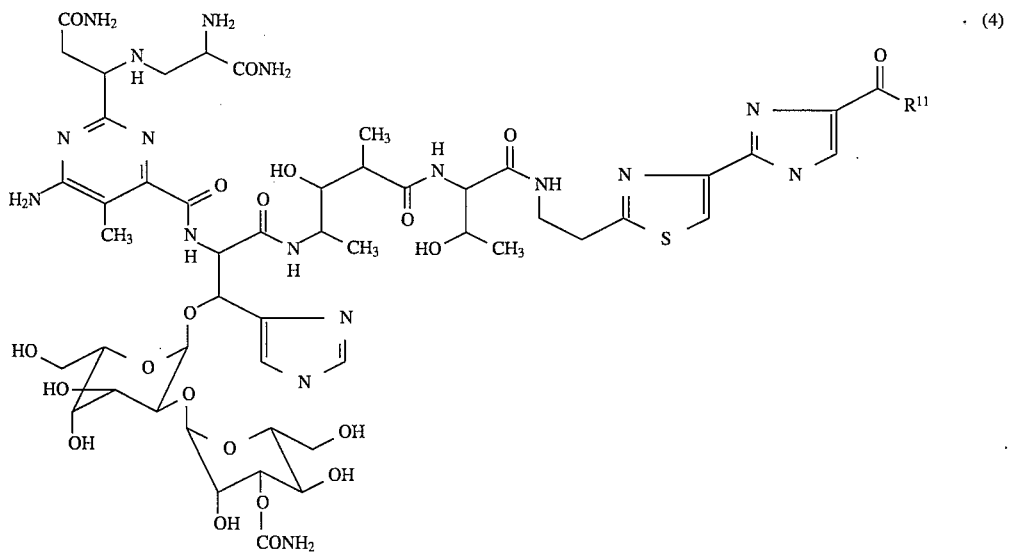

(4)

in which $R^{11}$ is hydroxy, amino, $C_1$–$C_3$ alkylamino, di($C_1$–$C_3$ alkyl)amino, $C_4$–$C_6$ polymethylene amino, $$-NHCH_2CH_2CH_2\overset{+}{S}-CH_3;$$
$$\phantom{-NHCH_2CH_2CH_2\overset{+}{S}}|$$
$$\phantom{-NHCH_2CH_2CH_2\overset{+}{S}-}CH_3$$

or $$-NHCH_2CH_2CH_2CH_2NH-\overset{\overset{NH}{\|}}{C}-NH_2;$$

MELPHALAN OF FORMULA (5):

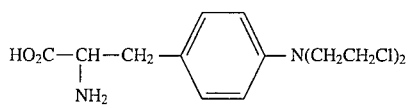
(5)

6-MERCAPTOPURINE OF FORMULA (6):

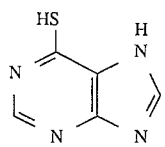
(6)

A CYTOSINE ARABINOSIDE OF FORMULA (7):

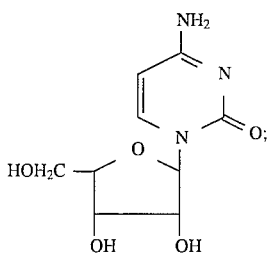
(7)

THE PODOPHYLLOTOXINS OF FORMULA (8):

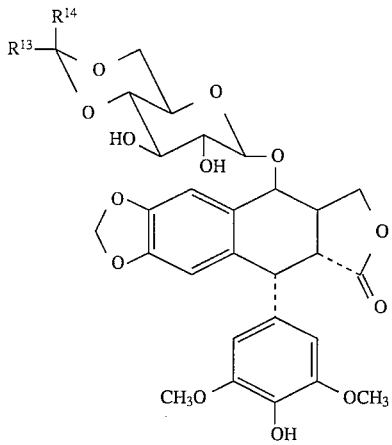
(8)

in which
$R^{13}$ is hydrogen or methyl;
$R^{14}$ is methyl or thienyl;
or a phosphate salt thereof;

THE VINCA ALKALOID GROUP OF DRUGS OF FORMULA (9):

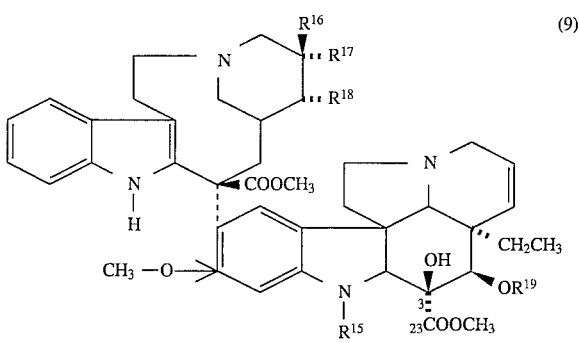
(9)

in which $R^{15}$ is H, $CH_3$ or CHO; when $R^{17}$ and
$R^{18}$ are taken singly, $R^{18}$ is H, and one of $R^{16}$ and $R^{17}$ is ethyl and the other is H or OH; when $R^{17}$ and $R^{18}$ are taken together with the carbons to which they are attached, they form an oxirane ring in which case $R^{16}$ is ethyl;

$R^{19}$ is hydrogen, $(C_1-C_3$ alkyl$)$—CO, or chlorosubstituted $(C_1-C_3$ alkyl$)$—CO;

DIFLUORONUCLEOSIDES OF FORMULA (10):

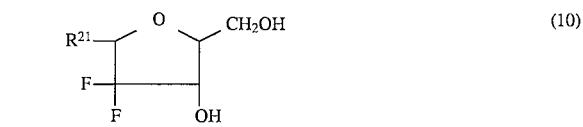
(10)

in which $R^{21}$ is a base of one of the formulae:

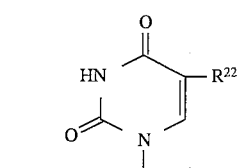

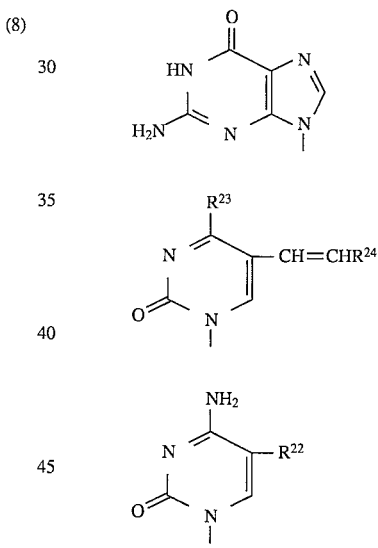

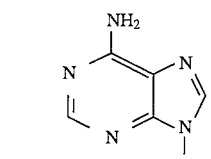

in which $R^{22}$ is hydrogen, methyl, bromo, fluoro, chloro or iodo;

$R^{23}$ is —OH or —$NH_2$;

$R^{24}$ is hydrogen, bromo, chloro or iodo; or,

THE ANTHRACYCLINES ANTIBIOTICS OF FORMULA (11):

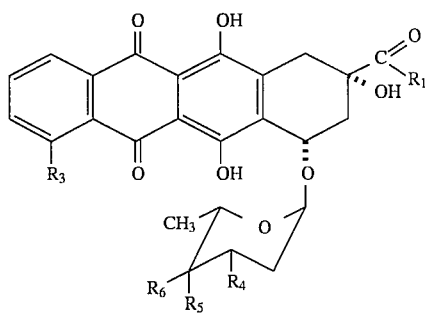

wherein $R_1$ is $-CH_3$, $-CH_2OH$, $-CH_2OCO(CH_2)_3CH_3$ or $-CH_2OCOCH(OC_2H_5)_2$ $R_3$ is $-OCH_3$, $-OH$ or $-H$ $R_4$ is $-NH_2$, $-NHCOCF_3$, 4-morpholinyl, 3-cyano-4-morpholinyl, 1-piperidinyl, 4-methoxy-1-piperidinyl, benzylamine, dibenzylamine, cyanomethylamine, or 1-cyano-2-methoxyethyl amine $R_5$ is $-OH$, $-OTHP$, or $-H$; and, $R_6$ is $-OH$ or $-H$ provided that $R_6$ is not $-OH$ when $R_5$ is $-OH$ or $-OTHP$.

The most highly preferred drugs are the anthracycline antibiotic agents of Formula (11), described previouly. One skilled in the art understands that this structural formula includes compounds which are drugs, or are derivatives of drugs, which have acquired in the art different generic or trivial names. Table I, which follows, represents a number of anthracycline drugs and their generic or trivial names and which are especially preferred for use in the present invention.

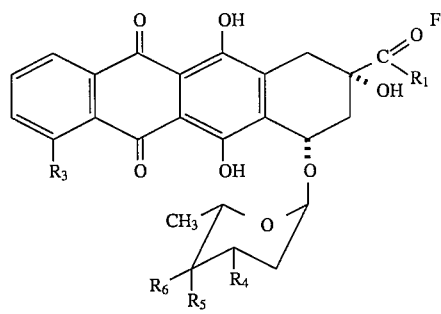

THE LIGANDS

One skilled in the art understands that "ligand" includes within its scope any molecule that specifically binds or reactively associates or complexes with a receptor or other receptive moiety associated with a given target cell population. This cell reactive molecule, to which the drug reagent is linked via the linker in the conjugate, can be any molecule that binds to, complexes with or reacts with the cell population sought to be therapeutically or otherwise biologically modified and, which possesses a free reactive sulfhydryl ($-SH$) group or can be modified to contain a such a sulfhydryl group. The cell reactive molecule acts to deliver the therapeutically active drug moiety to the particular target cell population with which the ligand reacts. Such molecules include, but are not limited to, large molecular weight proteins (generally greater than 10,000 daltons) such as, for example, antibodies, smaller molecular weight proteins (generally, less than 10,000 daltons), polypeptide or peptide ligands, and non-peptidyl ligands.

The non-immunoreactive protein, polypeptide, or peptide ligands which can be used to form the conjugates of this invention may include, but are not limited to, transferrin, epidermal growth factors ("EGF"), bombesin, gastrin, gastrin-releasing peptide, platelet-derived growth factor, IL-2, IL-6, tumor growth factors ("TGF"), such as TGF-α and TGF-β, vaccinia growth factor ("VGF"), insulin and insulin-like growth factors I and II. Non-peptidyl ligands may include, for example, steroids, carbohydrates and lectins.

The immunoreactive ligands comprise an antigen-recognizing immunoglobulin (also referred to as "antibody"), or antigen-recognizing fragment thereof. Particularly preferred immunoglobulins are those immunoglobulins which can recognize a tumor-associated antigen. As used, "immunoglobulin" may refer to any recognized class or subclass of immunoglobulins such as IgG, IgA, IgM, IgD, or IgE. Preferred are those immunoglobulins which fall within the IgG class of immunoglobulins. The immunoglobulin can be derived from any species. Preferably, however, the immunoglobulin is of human, murine, or rabbit origin. Further, the immunoglobulin may be polyclonal or monoclonal, preferably monoclonal.

As noted, one skilled in the art will appreciate that the invention also encompasses the use of antigen recognizing immunoglobulin fragments. Such immunoglobulin fragments may include, for example, the Fab', F(ab')$_2$, F$_v$, or Fab fragments, or other antigen recognizing immunoglobulin fragments. Such immunoglobulin fragments can be pre-

TABLE I

| Compound | $R_1$ | $R_3$ | $R_4$ | $R_5$ | $R_6$ |
|---|---|---|---|---|---|
| Daunorubicin[a] | $CH_3$ | $OCH_3$ | $NH_2$ | $OH$ | $H$ |
| Adriamycin[b] | $CH_2OH$ | $OCH_3$ | $NH_2$ | $OH$ | $H$ |
| Detorubicin | $CH_2OCOCH(OC_2H_5)_2$ | $OCH_3$ | $NH_2$ | $OH$ | $H$ |
| Carminomycin | $CH_3$ | $OH$ | $NH_2$ | $OH$ | $H$ |
| Idarubicin | $CH_3$ | $H$ | $NH_2$ | $OH$ | $H$ |
| Epirubicin | $CH_2OH$ | $OCH_3$ | $NH_2$ | $H$ | $OH$ |
| Esorubicin | $CH_2OH$ | $OCH_3$ | $NH_2$ | $H$ | $H$ |
| THP | $CH_2OH$ | $OCH_3$ | $NH_2$ | $OTHP$ | $H$ |
| AD-32 | $CH_2OCO(CH_2)_3CH_3$ | $OCH_3$ | $NHCOCF_3$ | $OH$ | $H$ |

[a]"Daunomycin" is an alternate name for daunorubicin
[b]"Doxorubicin" is an alternate name for adriamycin Of the compounds shown in Table I, the most highly preferred drug is adriamycin. Adriamycin (also referred to herein as "ADM") is that anthracycline of Formula (11) in which $R_1$ is $-CH_2OH$, $R_3$ is $-OCH_3$, $R_4$ is $-NH_2$, $R_5$ $-OH$, and $R_6$ is $-H$.

pared, for example, by proteolytic enzyme digestion, for example, by pepsin or papain digestion, reductive alkylation, or recombinant techniques. The materials and methods for preparing such immunoglobulin fragments are well-known to those skilled in the art. See generally, Parham, J.

*Immunology,* 131, 2895 (1983); Lamoyi et al., *J. Immunological Methods,* 56, 235 (1983); Parham, id., 53, 133 (1982); and Matthew et al., id., 50, 239 (1982).

The immunoglobulin can be a "chimeric antibody" as that term is recognized in the art. Also, the immunoglobulin may be a "bifunctional" or "hybrid" antibody, that is, an antibody which may have one arm having a specificity for one antigenic site, such as a tumor associated antigen while the other arm recognizes a different target, for example, a hapten which is, or to which is bound, an agent lethal to the antigen-bearing tumor cell. Alternatively, the bifunctional antibody may be one in which each arm has specificity for a different epitope of a tumor associated antigen of the cell to be therapeutically or biologically modified. In any case, the hybrid antibodies have a dual specificity, preferably with one or more binding sites specific for the hapten of choice or one or more binding sites specific for a target antigen, for example, an antigen associated with a tumor, an infectious organism, or other disease state.

Biological bifunctional antibodies are described, for example, in European Patent Publication, EPA 0 105 360, to which those skilled in the art are referred. Such hybrid or bifunctional antibodies may be derived, as noted, either biologically, by cell fusion techniques, or chemically, especially with cross-linking agents or disulfide bridge-forming reagents, and may be comprised of whole antibodies and/or fragments thereof. Methods for obtaining such hybrid antibodies are disclosed, for example, in PCT application W083/03679, published Oct. 27, 1983, and published European Application EPA 0 217 577, published Apr. 8, 1987, both of which are incorporated herein by reference. Particularly preferred bifunctional antibodies are those biologically prepared from a "polydoma" or "quadroma" or which are synthetically prepared with cross-linking agents such as bis-(maleimido)-methyl ether ("BMME"), or with other cross-linking agents familiar to those skilled in the art.

In addition the immunoglobin may be a single chain antibody ("SCA"). These may consist of single chain Fv fragments ("scFv") in which the variable light ("$V_L$") and variable heavy ("$V_H$") domains are linked by a peptide bridge or by disulfide bonds. Also, the immunoglobulin may consist of single $V_H$ domains (dAbs) which possess antigen-binding activity. See, e.g., G. Winter and C. Milstein, *Nature,* 349, 295 (1991); R. Glockshuber et al., *Biochemistry* 29, 1362 (1990); and, E. S. Ward et al., *Nature* 341, 544 (1989).

Especially preferred for use in the present invention are chimeric monoclonal antibodies, preferably those chimeric antibodies having specificity toward a tumor associated antigen. As used herein, the term "chimeric antibody" refers to a monoclonal antibody comprising a variable region, i.e. binding region, from one source or species and at least a portion of a constant region derived from a different source or species, usually prepared by recombinant DNA techniques. Chimeric antibodies comprising a murine variable region and a human constant region are especially preferred in certain applications of the invention, particularly human therapy, because such antibodies are readily prepared and may be less immunogenic than purely murine monoclonal antibodies. Such murine/human chimeric antibodies are the product of expressed immunoglobulin genes comprising DNA segments encoding murine immunoglobulin variable regions and DNA segments encoding human immunoglobulin constant regions. Other forms of chimeric antibodies encompassed by the invention are those in which the class or subclass has been modified or changed from that of the original antibody. Such "chimeric" antibodies are also referred to as "class-switched antibodies". Methods for producing chimeric antibodies involve conventional recombinant DNA and gene transfection techniques now well known in the art. See, e.g., Morrison, S. L, et al., *Proc. Nat'l Acad. Sci.,* 81, 6851 (1984).

Encompassed by the term "chimeric antibody" is the concept of "humanized antibody", that is those antibodies in which the framework or "complementarity determining regions ("CDR") have been modified to comprise the CDR of an immunoglobulin of different specificity as compared to that of the parent immunoglobulin. In a preferred embodiment, a murine CDR is grafted into the framework region of a human antibody to prepare the "humanized antibody". See, e.g., L. Riechmann et al., *Nature* 332, 323 (1988); M. S. Neuberger et al., *Nature* 314, 268 (1985). Particularly preferred CDR'S correspond to those representing sequences recognizing the antigens noted above for the chimeric and bifunctional antibodies. The reader is referred to the teaching of EPA 0 239 400 (published Sep. 30, 1987), incorporated herein by reference, for its teaching of CDR modified antibodies.

One skilled in the art will recognize that a bifunctional-chimeric antibody can be prepared which would have the benefits of lower immunogenicity of the chimeric or humanized antibody, as well as the flexibility, especially for therapeutic treatment, of the bifunctional antibodies described above. Such bifunctional-chimeric antibodies can be synthesized, for instance, by chemical synthesis using cross-linking agents and/or recombinant methods of the type described above. In any event, the present invention should not be construed as limited in scope by any particular method of production of an antibody whether bifunctional, chimeric, bifunctional-chimeric, humanized, or an antigen-recognizing fragment or derivative thereof.

In addition, the invention encompasses within its scope immunoglobulins (as defined above) or immunoglobulin fragments to which are fused active proteins, for example, an enzyme of the type disclosed in Neuberger, et al., PCT application, W086/01533, published Mar. 13, 1986. The disclosure of such products is incorporated herein by reference.

As noted, "bifunctional", "fused", "chimeric" (including humanized), and "bifunctional-chimeric" (including humanized) antibody constructions also include, within their individual contexts constructions comprising antigen recognizing fragments. As one skilled in the art will recognize, such fragments could be prepared by traditional enzymatic cleavage of intact bifunctional, chimeric, humanized, or chimeric-bifunctional antibodies. If, however, intact antibodies are not susceptible to such cleavage, because of the nature of the construction involved, the noted constructions can be prepared with immunoglobulin fragments used as the starting materials; or, if recombinant techniques are used, the DNA sequences, themselves, can be tailored to encode the desired "fragment" which, when expressed, can be combined in vivo or in vitro, by chemical or biological means, to prepare the final desired intact immunoglobulin "fragment". It is in this context, therefore, that the term "fragment" is used.

Furthermore, as noted above, the immunoglobulin (antibody), or fragment thereof, used in the present invention may be polyclonal or monoclonal in nature. Monoclonal antibodies are the preferred immunoglobulins, however. The preparation of such polyclonal or monoclonal antibodies now is well known to those skilled in the art who, of course, are fully capable of producing useful immunoglobulins which can be used in the invention. See, e.g., G. Kohler and C. Milstein, *Nature* 256, 495 (1975). In addition, hybridomas and/or monoclonal antibodies which are produced by such hybridomas and which are useful in the practice of the present invention are publicly available from sources such as the American Type Culture Collection ("ATCC") 12301 Parklawn Drive, Rockville, Md. 20852 or, commerically, for example, from Boehringer-Mannheim Biochemicals, P.O. Box 50816, Indianapolis, Ind. 46250.

Particularly preferred monoclonal antibodies for use in the present invention are those which recognize tumor associated antigens. Such monoclonal antibodies, are not to be so limited, however, and may include, for example, the following:

| Antigen Site Recognized | Monoclonal Antibodies | Reference |
|---|---|---|
| Lung Tumors | KS1/4 | N. M. Varki, et al., Cancer Res. 44:681, 1984 |
| | 534, F8; 604A9 | F. Cuttitta, et al., in: G. L. Wright (ed) Monoclonal Antibodies and Cancer, Marcel Dekker, Inc., NY., p. 161, 1984. |
| Squamous Lung | G1, LuCa2, LuCa3, LuCa4 | Kyoizumi et al., Cancer Res., 45:3274 1985. |
| Small Cell Lung Cancer | TFS-2 | Okabe et al., Cancer Res. 45:1930, 1985. |
| Colon Cancer | 11.285.14 14.95.55 | G. Rowland, et al., Cancer Immunol. Immunother., 19:1, 1985 |
| | NS-3a-22, NS-10 NS-19-9, NS-33a NS-52a, 17-1A | Z. Steplewski, et al., Cancer Res., 41:2723, 1981. |
| Carcino-embryonic | MoAb 35 or ZCE025 | Acolla, R. S. et al., Proc. Natl. Acad. Sci., (USA), 77:563, 1980. |
| Melanoma | 9.2.27 | T. F. Bumol and R. A. Reisfeld, Proc. Natl. Acad. Sci., (USA), 79:1245, 1982. |
| p97 | 96.5 | K. E. Hellstrom, et al., Monoclonal Antibodies and Cancer, loc. cit. p. 31. |
| Antigen T65 | T101 | Boehringer-Mannheim, P.O. Box 50816, Indianapolis, IN 46250 |
| Ferritin | Antiferrin | Boehringer-Mannheim, P.O. Box 50816, Indianapolis, IN 46250 |
| | R24 | W. G. Dippold, et al., Proc. Natl. Acad. Sci. (USA), 77:6114, 1980 |
| Neuroblastoma | P1 153/3 | R. H. Kennet and F. Gilbert, Science, 203:1120, 1979. |
| | MIN 1 | J. T. Kemshead in Monoclonal Antibodies and Cancer, loc. cit. p. 49. |
| | UJ13A | Goldman et al., Pediatrics, 105:252, 1984. |
| Glioma | BF7, GE2, CG12 | N. de Tribolet, et al., in Monoclonal Antibodies and Cancer, loc. cit. p. 81 |
| Ganglioside | L6 | I. Hellstrom et al. Proc. Natl Acad. Sci. (U.S.A) 83:7059 (1986); U.S. Pat. Nos. 4,906,562, issued March 6, 1990 and 4,935,495, issued June 19, 1990. |
| | Chimeric L6 | U.S. Ser. No. 07/923,244, filed Oct. 27, 1986, equivalent to PCT Patent Publication, WO 88/03145, published May 5, 1988. |
| Lewis Y | BR64 | U.S. Ser. Nos. 07/289,635, filed December 22, 1988, and U.S. Ser. No. 07/443,696, filed Nov. 29, 1989, equivalent to European Patent Publication, EP A 0 375 562, published June 27, 1990. |
| fucosylated Lewis Y | BR96, Chimeric BR96 | U.S. Ser. Nos. 07/374,947, filed June 30, 1989, and U.S. Ser. No. 07/544,246, filed June 26, 1990, equivalent to PCT Patent Publication, WO 91/00295, published January 10, 1991. |
| Breast Cancer | B6.2, B72.3 | D. Colcher, et al., in Monoclonal Antibodies and Cancer, loc. cit. p. 121. |
| Osteogenic Sarcoma | 791T/48, 791T/36 | M. J. Embleton, ibid, p. 181 |
| Leukemia | CALL 2 | C. T. Teng, et al., Lancet, 1:01, 1982 |
| | anti-idiotype | R. A. Miller, et al., N. Eng. J. Med., 306:517, 1982 |
| Ovarian Cancer | OC 125 | R. C. Bast, et al., J. Clin. Invest., 68:1331, 1981. |
| Prostrate Cancer | D83.21, P6.2, Turp-27 | J. J. Starling, et al., in Monoclonal Antibodies and Cancer, loc. cit., p. 253 |
| Renal Cancer | A6H, D5D | P. H. Lange, et al., Surgery, 98:143, 1985. |

In the most preferred embodiment, the ligand containing conjugate is derived from chimeric antibody BR96, "ChiBR96", disclosed in U.S. Ser. No. 08/057,444, filed May 5, 1993, which is a file wrapper continuation of U.S. Ser. No. 07/544,246, filed Jun. 26, 1990, now abandoned, and which is equivalent to PCT Published Application, WO 91/00295, published Jan. 10, 1991. ChiBR96 is an internalizing murine/human chimeric antibody and is reactive, as noted, with the fucosylated Lewis Y antigen expressed by human carcinoma cells such as those derived from breast, lung, colon, and ovarian carcinomas. The hybridoma expressing chimeric BR96 and identified as ChiBR96 was deposited on May 23, 1990, under the terms of the Budapest Treaty, with the American Type Culture Collection ("ATCC"), 12301 Parklawn Drive, Rockville, Md. 20852. Samples of this hybridoma are available under the accession number ATCC HB 10460. ChiBR96 is derived, in part, from its source parent, BR96. The hybridoma expressing BR96 was deposited, on Feb. 21, 1989, at the ATCC, under the terms of the Budapest Treaty, and is available under the accession number HB 10036. The desired hybridoma is cultured and the resulting antibodies are isolated from the cell culture supernatant using standard techniques now well known in the art. See, e.g., "Monoclonal Hybridoma Antibodies: Techniques and Applications", Hurell (ed.) (CRC Press, 1982).

In another highly preferred embodiment the immunoconjugate is derived from the BR64 murine monoclonal antibody disclosed in U.S. Ser. No. 07/289,635, filed Dec. 22, 1988, now abandoned, and, U.S. Ser. No. 07/443,696, filed Nov. 29, 1989, equivalent to European Published Application, EP A 0 375 562, published Jun. 27, 1990. As noted above, this antibody also is internalizing and is reactive with the Lewis Y antigen expressed by carcinoma cells derived from the human colon, breast, ovary and lung. The hybridoma expressing antibody BR64 and is identified as BR64 was deposited on Nov. 3, 1988, under the terms of the Budapest Treaty, with the ATCC and is available under the accession number HB 9895. The hybridoma is cultured and the desired antibody is isolated using standard techniques well known in the art, such as those referenced above.

In a third highly preferred embodiment, an immunoconjugate of the invention is derived from the L6 murine monoclonal antibody disclosed in U.S. Pat. No. 4,906,562, issued Mar. 6, 1990, and U.S. Pat. No. 4,935,495, issued Jun. 19, 1990. L6 is a non-internalizing antibody active against a ganglioside antigen expressed by human carcinoma cells derived from human non-small cell lung, breast, colon or ovarian carcinomas. The hybridoma expressing L6 and identified as L6 was deposited under the terms of the Budapest Treaty on Dec. 6, 1984 at the ATCC and is available under the accession number HB 8677. The hydridoma is cultured and the desired antibody is isolated using the standard techniques referenced above. A chimeric form of the L6 antibody, if desired, is described in U.S. Ser. No. 07/923,244, equivalent to PCT Published Application, WO 88/03145, published May 5, 1988.

Thus, as used "immunoglobulin" or "antibody" encompasses within its meaning all of the immunoglobulin/antibody forms or constructions noted above.

THE INTERMEDIATES AND THE CONJUGATES

The invention provides as intermediates a Michael Addition Receptor- and acylhydrazone-containing drug derivative of Formula (IIa):

[D=N—NHCO(CH$_2$)$_n$—R    (IIa)

in which D is a drug moiety, n is an integer from 1 to 10 and R is a Michael Addition Receptor, all of which are as defined above.

An especially preferred intermediate encompassed by Formula (IIa) and which is useful for preparation of a conjugate of the invention is one defined by Formula (IIb):

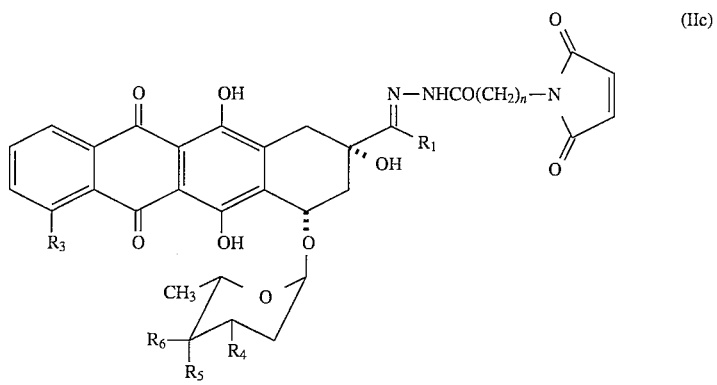

in which $R_1$ is —CH$_3$, —CH$_2$OH, —CH$_2$OCO(CH$_2$)$_3$CH$_3$ or —CH$_2$OCOCH(OC$_2$H$_5$)$_2$;

$R_3$ is —OCH$_3$, —OH or hydrogen;

$R_4$ is —NH$_2$, —NHCOCF$_3$, 4-morpholinyl, 3-cyano-4-morpholinyl, 1-piperidinyl, 4-methoxy-1-piperidinyl, benzylamine, dibenzylamine, cyanomethyl amine or 1-cyano-2-methoxyethyl amine.

$R_5$ is —OH, —OTHP or hydrogen;

$R_6$ is —OH or hydrogen, provided that $R_6$ is not —OH when $R_5$ is —OH or —OTHP;

n is an integer from 1 to 10; and,

R is a Michael Addition receptor moiety.

The most preferred intermediate for use in the present invention is defined by Formula (IIc):

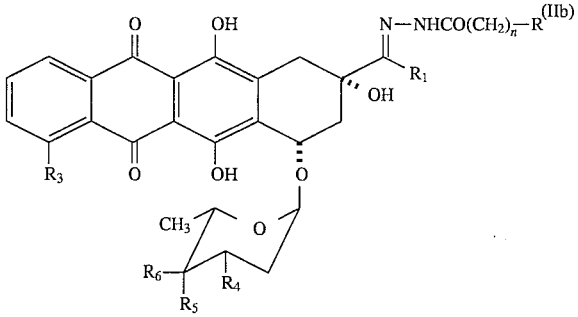

in which $R_1$, $R_3$, $R_4$, $R_5$ and $R_6$ are as defined above for Formula (IIb).

Also used as an intermediate in the invention is a targeting ligand which contains a freely reactive sulfhydryl group. The sulfhydryl group can be contained within the native targeting ligand or can be derived directly from the ligand or from a derivatized form of the ligand. In the preferred method for preparing the conjugates of the invention, a sulfhydryl group on the ligand or modified ligand reacts directly with the Michael Addition Receptor of intermediate of Formula (IIa) to form the final conjugate. Using this process, generally between about one and about ten drug molecules may be linked to each ligand. Thus, in Formula (I), q may be from about 1 to about 10.

When the conjugate is formed, the Michael Addition Receptor portion becomes a "Michael Addition Adduct", as used herein Thus, for example, as one skilled in the art will appreciate, if the Michael Addition Receptor moiety in the Formulae (IIa) or (IIb) compound is a maleimido moiety, the corresponding "Michael Addition Adduct" portion of the final conjugate of Formula (I) will be a succinimido moiety. Thus, a "Michael Addition Adduct" refers to a moiety which would be obtained had a Michael Addition Receptor, as defined in more detail below, undergone a Michael Addition reaction.

Thus, in a further embodiment of the invention, there is provided a process for preparing a compound of Formula (I), as defined above, which comprises reacting a compound of Formula (IIa), as defined above, with a ligand which contains, or is modified or derivatized to contain, a reactive sulfhydryl group, and if desired, isolating the product. This is the preferred method for preparing the compounds of Formula (I). Alternatively, the compounds of Formula (I) could be prepared by directly reacting the drug, or modified drug, with the acylhydrazide linker portion already covalently linked to the ligand, modified ligand, or deriva tized ligand. In particular, there is provided a process for preparing a compound of Formula (I):

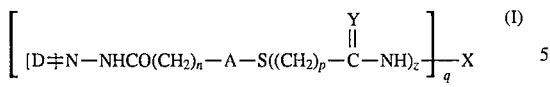

which comprises, (a) reacting a compound of Formula (IIa):

[D≑N—NHCO(CH$_2$)$_n$—R  (IIa)

with a compound of Formula (III):

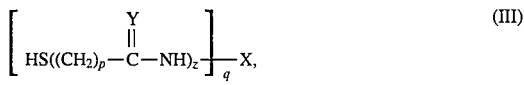

or;

(b) reacting a compound of the Formula:

[D—(C=O)]

with a compound of the Formula:

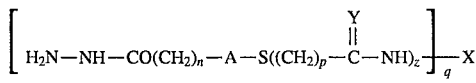

in which D, n, p, Y, z, q, X, R and A are as defined herein, and, if desired, isolating the product.

One skilled in the art understands that in the synthesis of compounds of the invention, one may need to protect or block various reactive functionalities on the starting compounds and intermediates while a desired reaction is carried out on other portions of the molecule. After the desired reactions are complete, or at any desired time, normally such protecting groups will be removed by, for example, hydrolytic or hydrogenolytic means. Such protection and deprotection steps are conventional in organic chemistry. One skilled in the art is referred to *Protective Groups in Organic Chemistry*, McOmie, ed., Plenum Press, New York, N.Y. (1973); and, *Protective Groups in Organic Synthesis*, Greene, ed., John Wiley & Sons, New York, N.Y., (1981) for the teaching of protective groups which may be useful in the preparation of compounds of the present invention.

By way of example only, useful amino-protecting groups may include, for example, $C_1$-$C_{10}$ alkanoyl groups such as formyl, acetyl, dichloroacetyl, propionyl, hexanoyl, 3,3-diethylhexanoyl, γ-chlorobutyryl, and the like; $C_1$-$C_{10}$ alkoxycarbonyl and $C_5$-$C_{15}$ aryloxycarbonyl groups such as tert-butoxycarbonyl, benzyloxycarbonyl, allyloxycarbonyl, 4-nitrobenzyloxycarbonyl and cinnamoyloxycarbonyl; halo-($C_1$-$C_{10}$)-alkoxycarbonyl such as 2,2,2-trichloroethoxycarbonyl; and $C_1$-$C_{15}$ arylalkyl and alkenyl groups such as benzyl, phenethyl, allyl, trityl, and the like. Other commonly used amino-protecting groups are those in the form of enamines prepared with β-keto-esters such as methyl or ethyl acetoacetate.

Useful carboxy-protecting groups may include, for example, $C_1$-$C_{10}$ alkyl groups such as methyl, tert-butyl, decyl; halo-$C_1$-$C_{10}$ alkyl such as 2,2,2-trichloroethyl, and 2-iodoethyl; $C_5$-$C_{15}$ arylalkyl such as benzyl, 4-methoxybenzyl, 4-nitrobenzyl, triphenylmethyl, diphenylmethyl; $C_1$-$C_{10}$ alkanoyloxymethyl such as acetoxymethyl, propionoxymethyl and the like; and groups such as phenacyl, 4-halophenacyl, allyl, dimethylallyl, tri($C_1$-$C_3$ alkyl)silyl, such as trimethylsilyl, β-p-toluenesulfonylethyl, β-p-nitrophenyl-thioethyl, 2,4,6-trimethylbenzyl, β-methylthioethyl, phthalimidomethyl, 2,4-dinitrophenylsulphenyl, 2-nitrobenzhydryl and related groups.

Similarly, useful hydroxy protecting groups may include, for example, the formyl group, the chloroacetyl group, the benzyl group, the benzhydryl group, the trityl group, the 4-nitrobenzyl group, the trimethylsilyl group, the phenacyl group, the tert-butyl group, the methoxymethyl group, the tetrahydropyranyl group, and the like.

In general, the intermediate Michael Addition Receptor containing hydrazone drug derivative of Formulae (IIa), (IIb), or (IIc) may be prepared, depending on the Michael Addition Receptor moiety used, by reaction of the drug (or derivatized drug) with a hydrazide containing a Michael Addition Receptor in the general manner described in Method A:

METHOD A

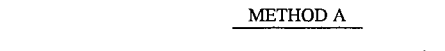

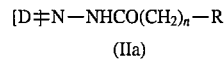

As noted below, Method A is the preferred method when the Michael Addition Receptor is a maleimido moiety.

Alternatively, the Formula (IIa) compound may be prepared by reaction of the drug with a hydrazide to form an intermediate hydrazone drug derivative followed by reaction of this compound with a Michael Addition Receptor containing moiety according to the general process described in Method B:

METHOD B

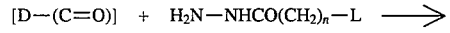

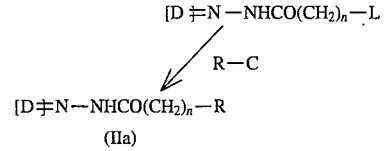

In Method A and Method B, D, n and R have the meanings previously noted. In Method B, L represents a leaving group, such as for example, halogen, mesylate or tosylate, capable of undergoing nucleophilic displacement while C represents a group which renders the Michael Addition Receptor, R, a good nucleophilic reagent. Particularly useful groups represented by C may include, for example, alkali metal ions such as $Na^+$, $K^+$ or $Li^+$.

A "Michael Addition Receptor", as one skilled in the art will understand, is a moiety capable reacting with a nucleophilic reagent so as to undergo a nucleophilic addition reaction characteristic of a Michael Addition reaction. As noted, after the nucleophilic addition occurs, the Michael Addition Receptor moiety is referred to as a "Michael Addition Adduct."

Michael Addition Receptors generally used in the Method A process may include, for example, α,β-ethylenic acids or α,β-thioacids such as those containing a —C=C—COOH, —C=C—C(O)SH, —C=C—C(S)SH, or a —C=C—C(S)OH moiety; α,β-ethylenic esters or thio-esters where the alkyl moiety is other than methyl or ethyl, for example, those which contain a —C=C—COOR, —C=C—C(S)OR, —C=C—C(S)SR, or —C=C—C(O)—SR moiety, wherein R is an ester forming group other than methyl or ethyl; α,β-ethylenic amides, imides, thioamides and thioimides (whether cyclic or acylic), for example, those which contain a moiety such as —C=C—CONR$_2$, —C=C—CONHCO—, —C=C—CSNR$_2$, —C=C—CSNHCO—, or —C=C—CSNHCS—, whether cyclic or acyclic and in which —CONR$_2$ or —CSNR$_2$ represents a primary, secondary, or tertiary amide or thioamide moiety; α,β-acetylenic acids or thioacids, for example, those containing a moiety such as —C≡C—COOH, —C≡C—C(S)OH, —C≡C—C(S)SH, or —C≡C—C(O)—SH; α,β-acetylenic esters, for example those which contain a moiety such as —C≡C—COOR, —C≡C—C(S)OR, —C≡C—C(S)SR, or —C≡C—C(O)—SR in which R is an ester forming group other than methyl or ethyl; α,β-ethylenic nitriles, for example those containing a moiety such as —C=C—C≡N; Michael Addition reactive cyclopropane derivatives, for example, 1-cyano-1-ethoxycarbonyl cyclopropane

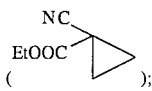
( );

a vinyl dimethyl-sulphonium bromide, for example, one containing a —C=C—S$^+$(Me)$_2$Br$^-$ moiety; an α,β-ethylenic sulfone, for example, one containing a

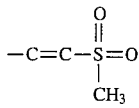

moiety; α,β-ethylenic nitro compounds, for example, one containing a —C=C—NO$_2$ moiety; α,β-ethylenic phosphonium compounds, for example one containing a

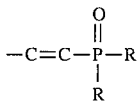

group; a compound containing a grouping such as C=C—C=N, as would be found, for example, in an aromatic heterocycle such as a 2- or 4-vinyl pyridine; or a compound containing an α,β-unsaturated thionium ion moiety, such as

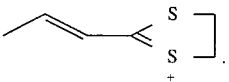

Michael Addition Receptors used in Method B may include α,β-ethylenic aldehydes, for example those compounds containing a —C=C—CHO moiety; α,β-ethylenic ketones, for example those compounds containing a

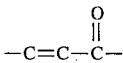

moiety; α,β-ethylenic esters or thio-esters such as compounds containing a —C=C—COOR, —C=C—C(S)OR, —C=C—C(S)SR, or —C=C—C(O)—SR moiety in which R is an ester-forming moiety which is methyl or ethyl, e.g.

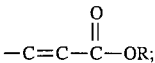

α,β-acetylenic aldehydes or ketones, for example compounds containing a —C≡CHO or —C=C—CO— moiety; α,β-acetylenic esters or thio-esters that have methyl or ethyl as their alkyl moiety, for example a compound containing a —C≡C—COOR, —C≡C—C(S)OR, —C≡C—C(O)SR or —C≡C—CSSR group in which R is an ester forming moiety which is methyl or ethyl.

One skilled in the art may be familiar with other Michael Addition Receptors which may be used in the present invention. For a general discussion of the Michael Addition Reaction, the reader is referred to E. D. Bergman, D. Ginsberg, and R. Pappo, *Org. React.* 10, 179–555 (1959); and, D. A. Oare and C. H. Heathcock, *Topics in Stereochemistry*, Vol. 20, eds., E. L. Eliel and S. H. Wilen, John Wiley and Sons, Inc. (1991), and references cited therein.

The precise reaction conditions used to prepare the intermediates of Formulae (IIa), (IIb), or (IIc) will depend upon the nature of the drug and the Michael Addition Receptor used in the reaction. The most preferred intermediate of the invention is that represented by Formula (IIc), above, in which the drug moiety is an anthracycline drug and the Michael Addition Receptor is a maleimido group. As noted earlier, for this reaction, Method A, described above, is used. Upon reaction with the ligand (thiolated, modified or otherwise), the maleimido Michael Addition Receptor of the intermediate becomes a succinimido group (the "Michael Addition Adduct") in the final conjugate.

The sulfhydryl containing ligands exist naturally (i.e. the ligand has not been modified) or may be produced, for example, (a) by thiolation of the ligand by reaction with a thiolating reagent such as SMCC or N-succinimid-yl-3-(2-pyridyldithio)propionate ("SPDP") followed by reduction of the product; (b) thiolation of the native ligand by reaction with iminothiolane ("IMT"); (c) addition of a sulfhydryl containing amino acid residue, for example, a cysteine residue, to the ligand should the ligand, for example, a protein peptide or polypeptide, fail to have a reactive and available sulfhydryl moiety; or, (d) reduction of a disulfide bond in a native molecule using a reducing agent useful for such purposes, for example, dithiothreitol ("DTT"). Method (d) is the most preferred method for production of sulfhydryl groups in antibody molecules used in the conjugates of the invention.

If a thiolating reagent such as SPDP or iminothiolane is used to prepare a conjugate of the invention, one skilled in the art will appreciate that a short "spacer" residue will be inserted between the Michael Addition Receptor moiety and the ligand in the conjugate of Formula (I). In such a case, z will be 1 in the Formula (I) compound. In the situation in which a free sulfhydryl group on the ligand is used directly, for example by use of a DTT reduced ligand (particularly a "relaxed" antibody prepared using for example, DTT), or in which a reactive residue, for example, cysteine is inserted into the ligand portion of the molecule, z in Formula (I) will be 0 and a direct thioether bond will exist between the binding ligand and the Michael Addition portion of the molecule.

Figure 14:
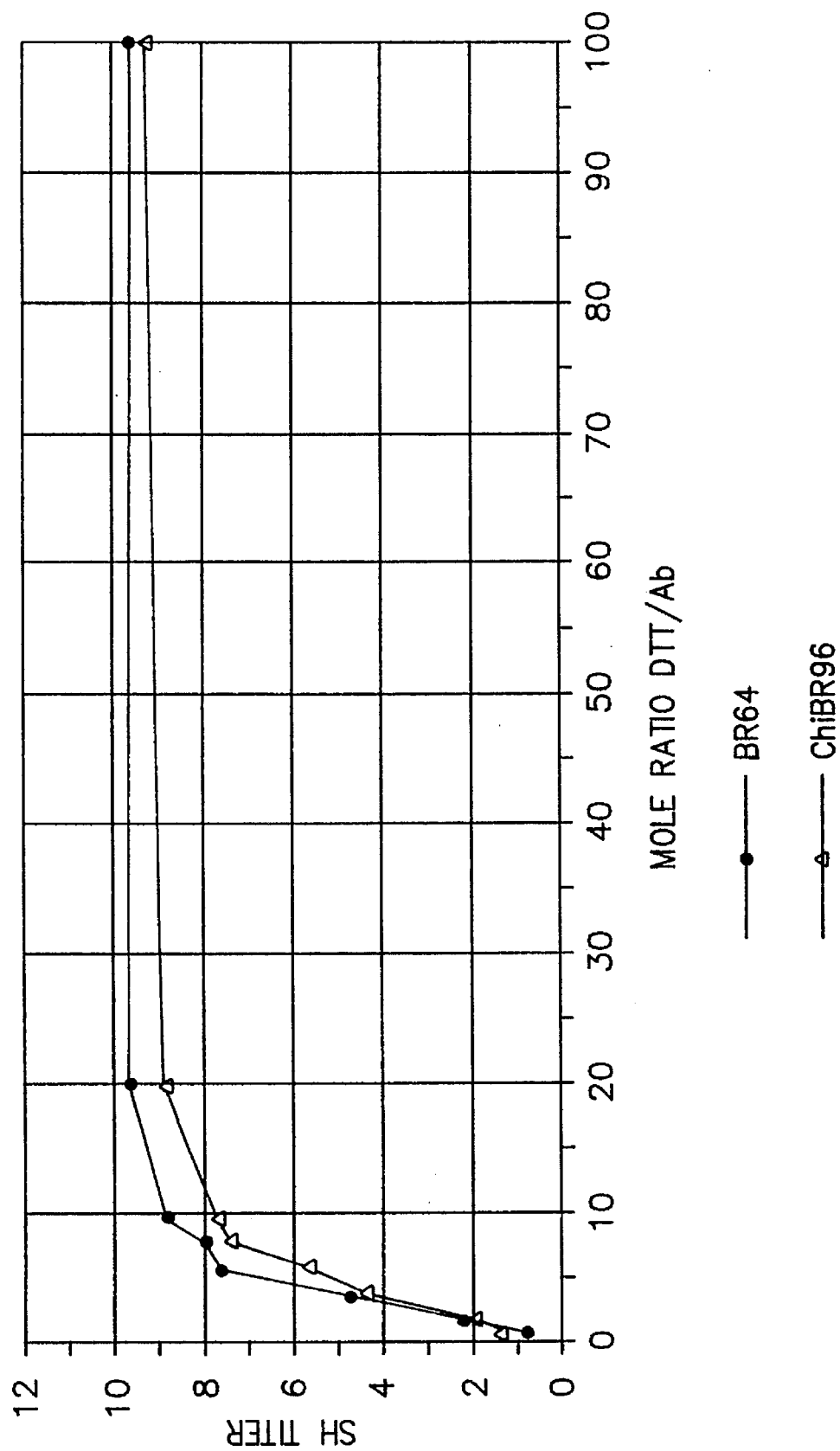
FIG. 14 provides a graph of the effect on —SH titer as a function of mole ratio of DTT to antibody in the preparation, under an inert atmosphere, of a relaxed antibody.

To form the conjugate, the thiolated ligand, or ligand having a freely reactive sulfhydryl group, is reacted with the Michael Addition Receptor containing hydrazone of Formula (IIa). In general, the reaction conditions must be chosen with regard to the stability of the ligand, the drug and the desired number of drug moieties to be linked to the ligand. For example, one skilled in the art will appreciate that the average number of drug molecules linked to the ligand can be varied by (1) modifying the amount of the intermediate drug-hydrazone of Formula (IIa) relative to the number of reactive sulfhydryl groups on the ligand moiety of the conjugate; or, (2) (a) modifying the number of reactive sulfhydryl groups on the ligand by, for example, only partially reducing the ligand (in the case of a protein, peptide or polypeptide), (b) by inserting a limited number of, for example, cysteine residues to a protein, peptide or polypeptide, or (c) by limiting the degree of thiolation using less than maximal amounts of thiolation agents, for example, SPDP or iminothiolane. Although the —SH titer can be varied, the preferred level of free sulfhydryl groups, particularly for a relaxed antibody, is the maximum obtainable using the particular reagents in question. The degree of variation in the —SH titer is easily controlled in the relaxed antibody process. For example, FIG. 14 shows the effect on —SH titer for antibodies BR64 and chimeric BR96 depending on the mole ratio of DTT to ligand, at 37° C., for a 1.5 hour reaction. One skilled in the art will appreciate that different classes or subclasses of immunoglobulins can have different numbers of disulfide bridges susceptible to reduction by reagents such as DTT. Thus, a further consideration in determining the desired level of conjugation of an antibody or antibody fragment is the number of disulfide groups available for reduction to free —SH groups. In general, however, the preferred conjugate of Formula (I) will have, on the average from a given reaction, from about 1 to about 10 drug molecules per ligand molecule. An especially preferred average drug to ligand molar ratio ("MR") is about 4 to about 8.

After the reaction of the conjugate is complete, the conjugate may be isolated and purified using commonly known dialysis, chromatographic and/or filtration methods. A final solution containing the conjugate customarily may be lyophilized to provide the conjugate in a dry, stable form which can be safely stored and shipped. The lyophilized product eventually can be reconstituted with sterile water or another suitable diluent for administration. Alternatively, the ultimate product may be frozen, for example under liquid nitrogen, and thawed and brought to ambient temperature prior to administration.

In a first preferred embodiment the anthracyclic hydrazone of Formula (IIa) is made by reacting the anthracycline with a maleimido-($C_1$–$C_{10}$)-alkyl hydrazide, or a salt thereof. This reaction is outlined in Method A, described earlier. The reaction generally is carried out in two steps. First the maleimido-($C_1$–$C_{10}$)-alkyl hydrazide, or its salt, is prepared. After purification by, for example, chromatography and/or crystallization, either the free base of the hydrazide or the salt are reacted with the desired anthracycline or anthracyline salt. After concentration of the reaction solution, the maleimido-containing hydrazone reaction product of Formula (IIa) is collected, and if desired, purified by standard purification techniques.

Figure 1B:
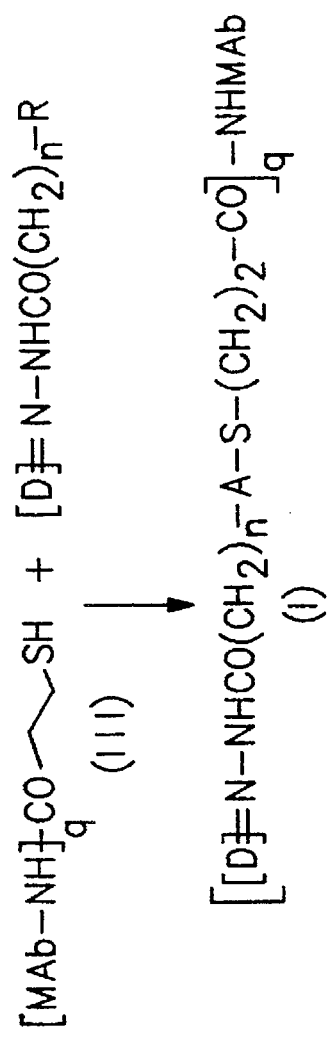

The Formula (IIa) hydrazone then is reacted with a sulfhydryl-containing antibody as described earlier. If the antibody is thiolated using, for example, N-succinimidyl-3-(2-pyridyldithio)propionate ("SPDP"), the thiolation reaction generally is performed in two steps: (1) Reaction of a free amino group on the antibody with SPDP; and, (2) DTT reduction of the SPDP disulfide to yield a free —SH group. In a preferred procedure, in Step (1) of the thiolation reaction, the SPDP/antibody molar ratio ranges between about 7.5:1 to about 60:1, depending upon the number of sulfhydryl groups desired, with a preferred range of about 7.5:1 to about 30:1, especially for BR64, and preferably about 20:1 for BR96. The reaction is carried out between about 0° C. and about 50° C., with a most preferred temperature of about 30° C. The reaction may be carried out at a pH range of between about 6 and about 8 with the most preferred pH being about 7.4. The reduction in Step (2), using preferably DTT, is performed using a DTT/SPDP molar ratio of between about 2.5:1 to about 10:1. The most preferred DTT/SPDP molar ratio is about 5:1 and the number of moles of SPDP is that which is added in Step (1) of the reaction. The reaction generally is carried out at about 0° C. to about 40° C., preferably 0° C. and is usually complete after about 20 minutes. After dialysis and concentration of the solution of thiolated ligand (an antibody in the most preferred embodiment), the molar concentration of sulfhydryl groups on the ligand is determined and the thiolated ligand is reacted with the desired molar ratio of the hydrazone derivative of Formula (IIa) relative to the molar amount of reactive sulfhydryl groups on the ligand. Preferably, the ratio is at least about 1:1. This reaction generally is performed at a temperature of about 0° C. to about 25° C., preferably about 4° C. The resulting conjugate then may be purified by standard methods. This reaction scheme is outlined in FIGS. 1a and 1b.

Figure 1C:
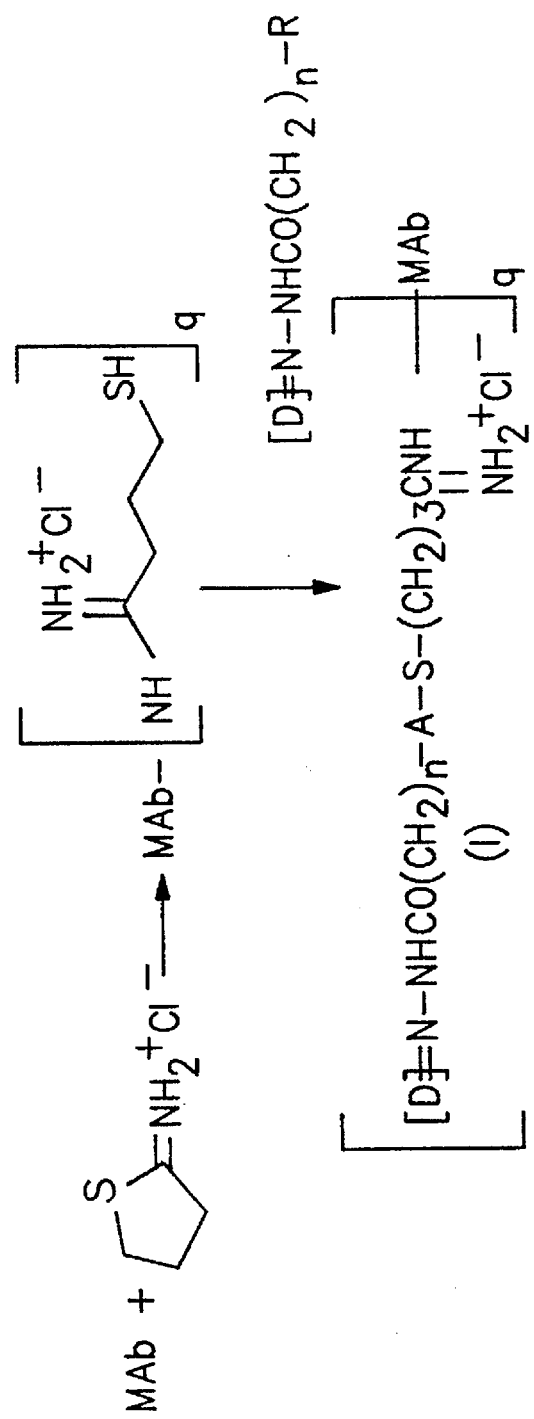
Figure 2:
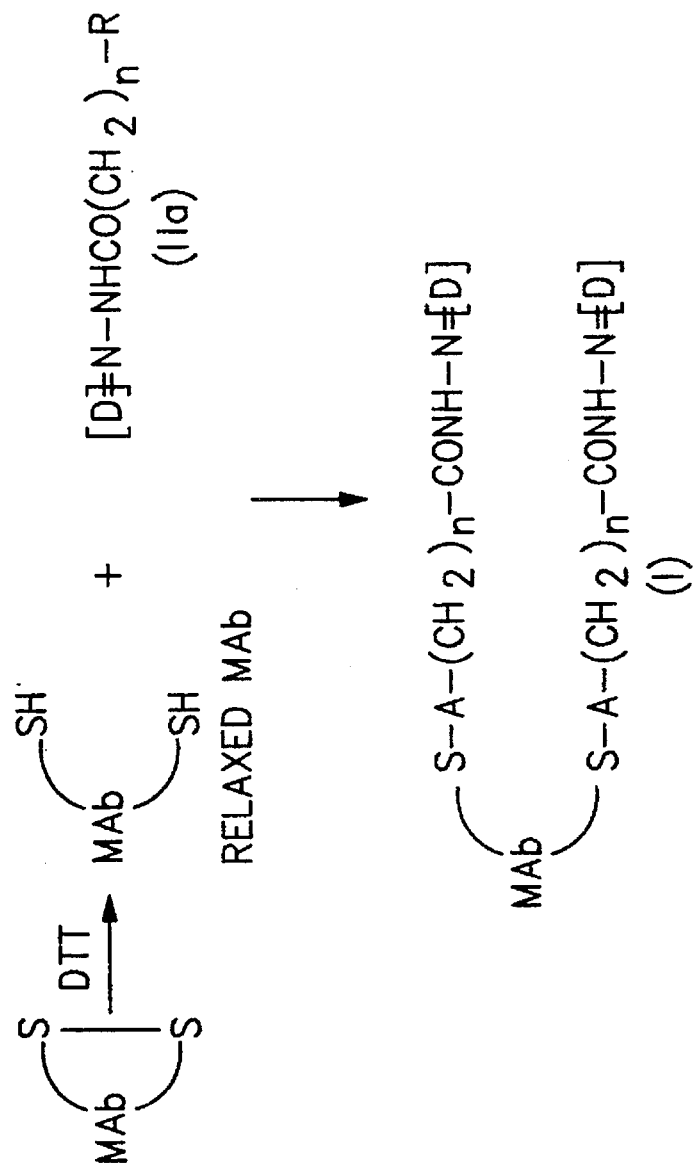
FIG. 2 shows a process for Reducing with DTT an antibody to prepare a "Relaxed" antibody and synthesis of an immunoconjugate of the invention.

In a second preferred embodiment, the hydrazone of Formula (IIa) is made as described above. The hydrazone then is reacted, as outlined in FIG. 1c, with an antibody which previously has been thiolated with iminothiolane ("IMT"). Thiolation of the ligand (preferably an antibody) with IMT generally is a one step reaction. The IMT/antibody ratio may range from between about 30:1 to about 80:1, preferably about 50:1. The reaction is performed for about 30 minutes to about 2 hours, preferably about 30 minutes, at a pH of about 7 to about 9.5, preferably at a pH of about 9, at a temperature of about 20° C. to about 40° C., preferably about 30° C. The reaction product then is reacted with the hydrazone of Formula (IIa) at a temperature of about 0° C. to about 25° C., preferably at about 4° C. and at a pH of about 7 to about 9.5, preferably about 7.4. The conjugate then is purified using methods standard in the art, for example, dialysis, filtration, or chromatography.

In a third especially preferred embodiment the intermediate hydrazone of Formula (IIa) is made as described above. The hydrazone then is reacted with a ligand, most preferably, an antibody, in which at least one disulfide group has been reduced to form at least one sulfhydryl group. An especially preferred ligand is a "relaxed antibody", as described below The preferred reducing agent for preparing a free sulfhydryl group is DTT although one skilled in the art will understand that other reducing agents may be suitable for this purpose.

A "relaxed" antibody, is one in which one or more, or preferably, three or more, disulfide bridges have been reduced. Most preferably, a relaxed antibody is one in which at least four disulfide bridges have been reduced. In a preferred process for preparing a relaxed (i.e. reduced) antibody, the reduction, especially with DTT, and the purification of the reaction product, is carried out in the absence of oxygen, under an inert atmosphere, for example, under nitrogen or argon. This process, as described in detail below, allows one to carefully control the degree of reduction. Thus, this process allows one skilled in the art to reproduce at any time the desired level of reduction of a ligand and, therefore, the number of free —SH groups available for preparing a conjugate of the invention.

In an alternative procedure, the reaction is carried out under ambient conditions, however, a sufficiently large amount of the reducing agent, preferably DTT, is used to overcome any reoxidation of the reduced disulfide bonds which may occur. In either case, purification of the product, is carried out as soon as possible after the reaction is complete and most preferably under an inert atmosphere such as an argon or nitrogen blanket. The preferred method for preparing the free sulfhydryl containing ligand, however, is the process in which atmospheric oxygen is excluded from the reaction. An antibody produced by either method is referred to as a "relaxed" antibody. The product, however prepared, should be used for subsequent reaction as quickly as possible or stored under conditions which avoid exposure to oxygen, preferably under an inert atmosphere.

In the process in which oxygen is excluded from the reaction (i.e. the reaction is performed under an inert atmosphere), the ligand is incubated, for a period of about 30 minutes to about 4 hours, preferably about 3 hours, with a molar excess of DTT. The DTT/ligand ratios may range between about 1:1 to about 20:1, preferably about 1:1 to about 10:1, most preferably about 7:1 to about 10:1, depending upon the number of sulfhydryl groups desired. For a reduction performed in the presence of oxygen, the mole ratio of DTT to ligand ranges from about 50:1 to about 400:1, preferably from about 200:1 to about 300:1. This latter reaction is carried out for about 1 to about 4 hours, preferably 1.5 hours, at a temperature of between about 20° C. and about 50° C., with a preferred temperature being about 37° C. The reaction is carried out at a pH of between about 6 and about 8, preferably between about 7 to 7.5. The product then is purified using standard purification techniques such as dialysis, filtration and/or chromatography. A preferred purification method is diafiltration. To prevent reoxidation of —SH groups, during purification and storage, the product preferably is maintained under an inert atmosphere to exclude exposure to oxygen.

One skilled in the art will appreciate that different ligands, particularly an antibody, may possess different degrees of susceptibility to reduction and/or reoxidation. Consequently, the conditions for reduction described above may need to be modified in order to obtain a given reduced ligand such as that desribed above. Furthermore, alternate means for preparing a reduced antibody useful in the conjugation process will be evident to one skilled in the art. Thus, however prepared, a reduced ligand used in the preparation of a conjugate of Formula (I) is meant to be encompassed by the present invention.

To prepare a conjugate of Formula (I), as noted earlier, the reduced antibody reaction product is reacted with the hydrazone intermediate of Formula (IIc). The reaction preferably is performed under an inert atmosphere at a temperature of about 0° C. to about 10° C., preferably at about 4° C. and at a pH of about 6 to about 8, preferably about 7.4. The immunoconjugate is purified using standard techniques such as dialysis, filtration, or chromatography.

In another embodiment of the invention, an anthracycline of Formula (11) is joined to a ligand to which is added a moiety carrying a free sulfhydryl group. In one such embodiment, the ligand is a non-antibody ligand, for example, bombesin. The sulfhydryl may be, for example, part of a cysteine residue added to the native bombesin molecule. The anthracycline is joined through a hydrazone moiety to a Michael Addition Receptor containing moiety which then reacts with the modified bombesin to form a conjugate of Formula (I). The product then is purified with standard techniques such as dialysis, centrifugation, or chromatography.

In a further embodiment, there is provided a method for the treatment of a disease or modification of a biological function which comprises administering to a warm-blooded animal in need thereof, a therapeutically effective or biological function modifying amount of a conjugate of Formula (I). As can be appreciated, the particular conjugate used will depend on the disease state to be treated or the biological system to be modified. In particular, one skilled in the art will be able to select a particular ligand and drug to prepare a conjugate of Formula (I) which has specificity for the treatment of the disease or is able to modify the biological function desired.

In a preferred embodiment, there is provided a method for the treatment of a neoplastic disease which comprises administering to a warm-blooded animal in need thereof a therapeutically effective amount of a cytotoxic conjugate of Formula (I). A particularly preferred conjugate for this purpose is an immunoconjugate of Formula (Ia):

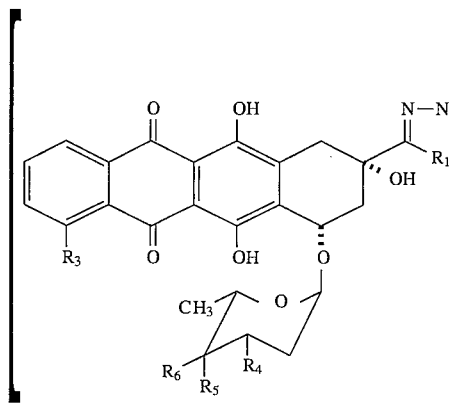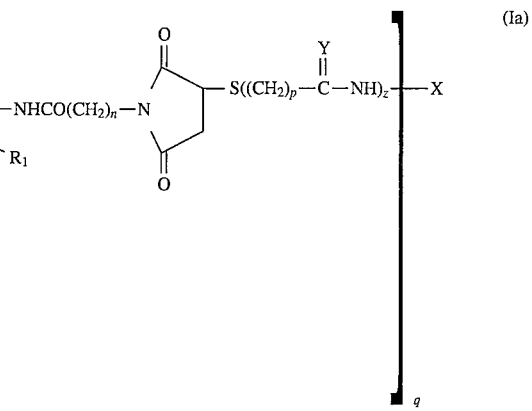

(Ia)

in which n, p, q, z, X, $R_1$, $R_3$, $R_4$, $R_5$, and $R_6$ are as previously defined.

The most preferred aspect of this latter embodiment is an immunoconjugate of Formula (Ia) in which the drug moiety is adriamycin and the ligand portion is selected from the group consisting of BR64, BR96, L6, chimeric BR64, chimeric BR96, chimeric L6 and the antigen-recognizing fragments thereof. The most preferred ligand for this embodiment is chimeric BR96, especially relaxed chimeric BR96, and the antigen-recognizing fragments thereof.

The conjugates of the invention are administered to the patient in the form of a pharmaceutical formulation which comprises a conjugate of Formula (I) and a pharmaceutically acceptable carrier, excipient or diluent therefor. As used, "pharmaceutically acceptable" refers to those agents which are useful in the treatment or diagnosis of a warm-blooded animal including, for example, a human, equine, porcine, bovine, murine, canine, feline, or other mammal, as well as an avian or other warm-blooded animal. The preferred mode of administration is parenterally, particularly by the intravenous, intramuscular, subcutaneous, intraperitoneal, or intralymphatic route. Such formulations can be prepared using carriers, diluents or excipients familiar to one skilled in the art. In this regard, See, e.g. Remington's Pharmaceutical Sciences, 16th ed., 1980, Mack Publishing Company, edited by Osol et al. Such compositions may include proteins, such as serum proteins, for example, human serum albumin, buffers or buffering substances such as phosphates, other salts, or electrolytes, and the like. Suitable diluents may include, for example, sterile water, isotonic saline, dilute aqueous dextrose, a polyhydric alcohol or mixtures of such alcohols, for example, glycerin, propylene glycol, polyethylene glycol and the like. The formulations may contain preservatives such as phenethyl alcohol, methyl and propyl parabens, thimerosal, and the like. If desired, the formulation can include 0.05 to about 0.20 percent by weight of an antioxidant such as sodium metabisulfite or sodium bisulfite.

For intravenous administration, the formulation preferably will be prepared so that the amount administered to the patient will be from about 0.01 to about 1 g of the desired conjugate. Preferably, the amount administered will be in the range of about 0.2 g to about 1 g of the conjugate. The conjugates of the invention are effective over a wide dosage range depending on factors such as the disease state to be treated or the biological effect to be modified, the manner in which the conjugate is administered, the age, weight and condition of the patient as well as other factors to be determined by the treating physician. Thus, the amount administered to any given patient must be determined on an individual basis.

One skilled in the art will appreciate that although specific reagents and reaction conditions are outlined in the following Preparations and Examples, modifications can be made which are meant to be encompassed by the spirit and scope of the invention. The following Preparations and Examples, therefore, are provided to further illustrate the invention.

PREPARATION 1

2,5-Dihydro-2,5-Dioxo-1H-Pyrrolo-1-Hexanoic Acid Hydrazide and its Trifluoroacetic Acid Salt ("Maleimidocaproyl Hydrazide")

Maleimidocaproic acid (2.11 g, 10 mmol) [See, e.g., D. Rich et al., *J. Med. Chem.*, 18, 1004 (1975); and, O. Keller, et al., *Helv. Chim. Acta*, 58 531 (1975)] was dissolved in dry tetrahydrofuran (200 mL). The solution was stirred under nitrogen, cooled to 4° C. and treated with N-methylmorpholine (1.01 g, 10 mmol) followed by dropwise addition of a solution of isobutyl chloroformate (1.36 g, 10 mmol) in THF (10 mL). After 5 min a solution of t-butyl carbazate (1.32 g, 10 mmol) in THF (10 mL) was added dropwise. The reaction mixture was kept at 4° C. for a half hour and at room temperature for 1 hour. The solvent was evaporated and the residue partitioned between ethyl acetate and water. The organic layer was washed with dilute HCl solution, water and dilute bicarbonate solution, dried over anhydrous sodium sulfate and the solvent evaporated. The material was purified by flash chromatography using a gradient solvent system of methylene chloride:methanol (100:1–2). The protected hydrazide was obtained in 70% yield (2.24 g).

This material (545 mg, 2.4 mmol) was dissolved and stirred in trifluoroacetic acid at 0°–4° C. for 8 min. The acid was removed under high vacuum at room temperature. The residue was triturated with ether to yield a crystalline trifluoroacetic acid salt of maleimidocaproyl hydrazide (384 mg, 70%). An analytical sample was prepared by crystallization from methanol-ether, to prepare the product, mp 102°–105° C.

The NMR and MS were consistent with structure. Anal: Calc'd. for $C_{10}H_{15}N_3O_3 \cdot 0.8CF_3COOH$: C, 44.02; H, 4.99; N, 13.28. Found (duplicate analyses): C, 44.16, 44.13; H, 4.97, 5.00; N, 12.74, 12.75.

The salt (220 mg) was converted to the free base by chromatography over silica using a methylene chloride:methanol:concentrated $NH_4OH$ (100:5:0.5) solvent system. The material obtained (124 mg, 80%) was crystallized from methylene chloride-ether to prepare a final product, mp 92°–93° C. NMR and MS were consistent with the structure. Anal: Calc'd. for $C_{10}H_{15}N_3O_3$: C, 53.33; H, 6.67; N, 18.67. Found: C, 53.12; H, 6.67; N, 18.44.

PREPARATION 2

Maleimidocaproylhydrazone of Adriamycin

A mixture of adriamycin hydrochloride (44 mg, 0.075 mmol), maleimidocaproyl hydrazide (23 mg, 0.102 mmol), prepared according to the procedure outlined in Preparation 1, and 2–3 drops of trifluoroacetic acid in absolute methanol (25 mL) was stirred for 15 hours under nitrogen and protected from light. At the end of this period no free adriamycin was detected by HPLC (mobile phase 0.01 molar ammonium acetate:acetonitrile, (70:30)). The solution was concentrated at room temperature under vacuum to 10 mL and diluted with acetonitrile. The clear solution was concentrated to a small volume, the solid was collected by centrifugation, and the product was dried under high vacuum to yield the title compound. The NMR was consistent with structure. High Resolution MS, calc'd. for $C_{31}H_{42}N_4O_{13}$: 751.2827; Found 751.2804.

The hydrazone also was formed by using adriamycin and the trifluoroacetic acid salt of the hydrazide. Thus, the salt (40 mg, 0.12 mmol), prepared according to the process outlined in Procedure 1, and adriamycin hydrochloride (50 mg, 0.086 mmol) were stirred in methanol (30 mL) for 15 hrs. The solution was concentrated to 2 mL and diluted with acetonitrile. The red solid was collected by centrifugation and dried under vacuum. The product (28 mg, 43%) was identical in NMR and TLC to the one described above. High Resolution MS calc'd. for $C_{31}H_{42}N_4O_{13}$: 751.2827; found 751.2819.

EXAMPLE 1A

Conjugate of SPDP Thiolated Monoclonal Antibody BR64 with the Maleimidocaproylhydrazone of Adriamycin A solution of the BR64 antibody (25 mL, 10.37 mg/mL; determined by UV at 280 nm, 1.4 absorbance units equal 1 mg protein) was treated with SPDP solution in absolute ethanol (1.3 mL of 10 mmol solution). The solution was incubated for 1 hour at 31°–32° C., then chilled in ice and treated with a solution of DTT in phosphate buffered saline ("PBS") (1.3 mL of a 50 mmol solution). The solution was kept in ice for 1 hour then transferred to a dialysis tube and dialyzed three times against PBS (2 L per dialysis) for a period of at least 8 hours. After the dialysis, the concentration of protein was measured, as above, followed by a determination of molar concentration of free sulfhydryl groups by the Ellman method.

The thiolated protein (3 mL) was treated with an equivalent thiol molar amount of maleimidocaproylhydrazone of adriamycin, prepared as in Preparation 2, dissolved in dimethylformamide (DMF) (5 mg/mL, 0.131 mL) and the mixture was incubated at 4° C. for 24 hours. The solution was dialyzed three times against PBS (1000 mL) for a period of at least 8 hours. The solution was centrifuged and the supernatant was shaken for a few hours with Bio-beads™ SM-2 (non-polar neutral macroporous polystyrene polymer beads, Bio-Rad Laboratories, Richmond, Calif. 94804) and finally filtered through a Millex-GV (Millipore Corporation, Bedford, Mass. 01730) 0.22 μm filter unit. The overall average number of molecules of adriamycin per molecule of antibody ("MR") was determined by measuring the amount of adriamycin from the absorption at 495 nm ($\epsilon=8030$ cm$^{-1}$M$^{-1}$) and the amount of protein from the absorption at 280 nm, after correcting for the absorption of adriamycin at 280 nm according to the formula:

$$\text{Antibody (mg/mL)} = \frac{A_{280} - (0.724 \times A_{495})}{1.4}$$

The MR found for the product was 5.38; free adriamycin 0.14%; protein yield 60%.

EXAMPLE 1B

Conjugate of SPDP Thiolated BR64 with the Maleimidocaproylhydrazone of Adriamycin A solution of the BR64 antibody (405 mL, 11.29 mg/mL) was stirred and treated with SPDP solution in absolute ethanol (22.3 mL of 10 mmol solution). The solution was incubated for 1 hour at 31°14 32° C. while being gently shaken, then cooled in ice to 4° C., stirred and treated with a solution of DTT in PBS (22.3 mL of a 50 mmol solution). The solution was kept in ice for 1 hour then divided into 2 equal parts, each transferred to a dialysis tube and dialyzed six times against PBS (6 L per dialysis) for a period of at least 8 hours. After that the contents of the tubes were combined (400 mL) and the concentration of protein and free thiol groups was determined (molar ratio of —SH groups to protein is 8.5).

The solution of thiolated protein was stirred and treated with an equivalent thiol molar amount of maleimidocaproyl hydrazone of adriamycin dissolved in DMF (5 mg/mL, 35.7 mL) and the mixture was incubated at 4° C. for 24 hours. The solution was divided into 2 equal parts, transferred to dialysis tubes and dialyzed five times against PBS (6 L per dialysis) for a period of at least 8 hours. The contents of the dialysis tubes were combined, filtered through a 0.22μ cellulose acetate filter, and the filtrate was shaken for 24 hours with Bio-beads™ SM-2 (Bio-Rad Laboratories, Richmond, Calif. 94804). The solution was filtered through a 0.22μ cellulose acetate filter. The concentration of protein and adriamycin was determined (6.26 mg/mL and 162.4 μg/mL, respectively) yielding a molar ratio (MR) of 7.18. The protein yield was 77%. Unconjugated adriamycin present was 0.07%.

EXAMPLE 2

Conjugate of SPDP Thiolated SN7 with the Maleimidocaproylhydrazone of Adriamycin In a manner analogous to that described in Examples 1A and 1B, monoclonal antibody SN7, an antibody which does not bind to the antigen recognized by BR64, was thiolated with SPDP and reacted with the maleimidocaproyl hydrazone of adriamycin to yield a conjugate with a molar ratio (MR) of 4. Protein yield was 51%. Unconjugated adriamycin present was 0.36%.

EXAMPLE 3

Conjugate of SPDP Thiolated ChiBR96 with the Maleimidocaproylydrazone of adriamycin A solution of chimeric BR96 antibody, ChiBR96, (27.5 mL, 12.53 mg/mL) was treated with a 10 mM solution of SPDP in absolute ethanol (1.7 mL). The solution was incubated at 31° C. for 35 minutes, chilled in ice and treated with a 0.50 mM solution of DTT in PBS (1.7 mL) for 15 min at 4° C. The solution was transferred to a dialysis tube and dialyzed four times in PBS-0.1M histidine buffer (4.5 L per dialysis) for a period of at least 8 hours. The amount of protein and molar concentration of thiol groups was determined (9.29 mg/mL and 2.06×10$^{-4}$M, respectively). The solution (17 mL) was treated with an equivalent molar amount of the maleimidocaproylhydrazone of adriamycin in DMF (5 mg/mL, 0.59 mL) and the reaction mixture incubated at 4° C. for 24 hours. The reaction mixture was dialyzed three times, in the same buffer (4.5 L per dialysis), for at least 8 hours. The dialyzed solution was centrifuged and the supernatant shaken gently with Biobeads™ SM-2 (Bio-Rad Laboratories, Richmond, Calif. 94804) for a few hours at 4° C. The solution was centrifuged and the concentration of protein and adriamycin in the supernatant (19 mL) was determined (6.5 mg/mL and 67.86 μg/mL, respectively). The molar ratio of drug to protein is 2.9. Protein yield is 72%; unconjugated adriamycin present is 1.2%.

EXAMPLE 4

Conjugation of Modified Bombesin with the Maleimidocaproylhydrazone of Adriamycin Bombesin does not contain a free reactive sulfhydryl group which can be used to link the drug through the Michael Addition Receptor-containing linker. Thus, there was prepared a modified bombesin which contains an additional cysteine residue at the amino terminus of native bombesin. In addition, residue-3 of the native bombesin has been changed to a lysine residue. The modified bombesin, therefore, is designated "Cys$^0$-lys$^3$-bombesin".

Cys$^0$-lys$^3$-bombesin (11.3 mg) was dissolved in 1.1 mL of deionized water and adjusted to pH 7–7.5 with 10 μl 1.5M Tris-HCl, pH 8.8 and then reacted with 0.45 mL maleimidocaproyl adriamycin hydrazone (15 mg/mL in deionized water) at ambient temperature for several hours. The reaction mixture was dialyzed against water overnight in dialysis tubing (molecular weight cutoff: 1000). The precipitate was removed by centrifugation (12,000×g) and the supernatant was saved. Adriamycin ("ADM") content of the bombesinadriamycin conjugate was measured by diluting 1:50 in acetate buffer, pH 6.0. The adriamycin ("ADM") content was calculated using the formula:

$$[O.D._{495}/8030] \times 50 = ADM \tag{M}$$

For this preparation O.D.$_{495}$=0.116 thus the adriamycin content was 7.2×10$^{-4}$M.

The product was chromatographed by HPLC using a C$_{18}$ (Beckman Instruments, Ultrasphere 5μ, 4.6 mm×25 cm) column. Buffer A: 10 mM NH$_4$OAc pH 4.5; Buffer B: 90% acetonitrile/10% Buffer A. The column was equilibrated with 90% Buffer A/10% Buffer B and the chromatography conditions were: 90% buffer A/10% buffer B to 60% Buffer A/60% buffer B for 2 minutes, gradient to 50% buffer A/50% buffer B for 15 minutes. The product had a retention time of 9.3 minutes under these conditions.

EXAMPLE 5

A Conjugate of Iminothiolane Thiolated Chimeric BR96 and Maleimidocaproyl Hydrazone of Adriamycin Chimeric BR96 (15 mL, 9.05 mg/mL) was dialysed two times against 4 liters of 0.1M sodium carbonate/bicarbonate buffer, pH 9.1. The antibody solution then was heated with iminothiolane (0.75 mL, 20 mM) at 32° C. for 45 minutes. The solution was then dialysed against 4 liters of sodium carbonate/bicarbonate buffer, pH 9.1 followed by dialysis against 4 liters of 0.0095M PBS-0.1M L-histidine, pH 7.4. This solution had a molar ratio of —SH/protein of 1.35. The protein then was re-thiolated as described above to yield a solution with a molar ratio of —SH/protein of 5.0.

The maleimidocaproyl hydrazone of adriamycin (3.2 mg in 0.640 mL DMF) was added with stirring at 4° C. to the thiolated protein solution. The conjugate was incubated at 4° C. for 16 hrs then it was dialysed against 4 liters of 0.0095M PBS-0.1M L-histidine, pH 7.4. The dialysed conjugate was filtered through a 0.22µ cellulose acetate membrane into a sterile tube to which a small quantity (>5% (v/v)) of Bio-Beads™ SM-2 (Bio-Rad Laboratories, Richmond, Calif. 94804) were added. After 24 hrs of gentle agitation, the beads were filtered off and the conjugate was frozen in liquid nitrogen and stored at −80° C. The resulting conjugate had a molar ratio of 3.4 adriamycin molecules to 1 molecule of protein and was obtained in 24% yield from chimeric BR96.

EXAMPLE 6

Conjugate of Maleimidocaproyl Hydrazone of Adriamycin with DTT reduced Human IgG ("Relaxed Human IgG")

Human IgG (obtained from Rockland, Gilbertsville, Pa.) was diluted with 0.0095M PBS to a protein concentration of 10.98 mg/mL. This solution (350 mL) was heated to 37° C. in a water bath under a nitrogen atmosphere. Dithiothreitol (16.8 mL, 10 mM) in PBS was added and the solution was stirred for 3 hrs at 37° C. The solution was divided equally between two Amicon (Amicon Division of W. R. Grace and Co., Beverly, Mass. 01915) Model 8400 Stirred Ultrafiltration Cells, each fitted with an Amicon YM 30 Ultrafilter membrane (MW cutoff 30,000, 76 mm diam.) and connected via an Amicon Model CDS10 concentration/dialysis selector to an Amicon Model RC800 mini-reservoir. Each reservoir contained 700 mL of 0.0095M PBS-0.1M L-histidine. The protein solutions were dialyzed until concentration of free thiol in the filtrate was 41 µM. The molar ratio of —SH/protein in the retentate was determined to be 8.13.

The retentate was transferred from the cells to a sterile container maintained under a nitrogen atmosphere and a solution of maleimidocaproyl hydrazone of adriamycin (36.7 mL, 5 mg/mL in water) was added with stirring. The conjugate was incubated at 4° C. for 48 hrs after which it was filtered through a 0.22µ cellulose acetate membrane. A Bio-Rad Econocolumn™ (2.5 cm×50 cm, Bio-Rad Laboratories, Richmond, Calif. 94804) was packed with a slurry of 100 g of BioBeads™ SM-2 (Bio-Rad Laboratories, Richmond, Calif. 94804) in 0.00095M-0.1M L-histidine buffer. The beads had been prepared by washing in methanol, followed by water and then several volumes of buffer. The filtered conjugate was percolated through this column at 2 mL/min. After chromatography the conjugate was filtered through a 0.22µ cellulose acetate membrane and frozen in liquid nitrogen and stored at −80° C. The conjugate obtained had an average molar ratio of 7.45 molecules of adriamycin per molecule of protein and was obtained in 99% yield from human IgG.

EXAMPLE 7

Conjugate of Relaxed BR64 with Maleimidocaproyl Hydrazone of Adriamycin

A solution of BR64 (435 mL; 11.31 mg/mL, 7.07×10$^{-5}$M) was treated with DTT (947 mg) and heated at 42°–43° C. with gentle stirring for 2 hrs. The solution was cooled in ice, transferred into 2 dialysis tubes and each tube was dialyzed 5 times against PBS (14 L per dialysis) for 8 hrs at 4° C. The contents of the tubes were combined (400 mL) and the protein and —SH content determined (10.54 mg/mL, 6.58× 10$^{-5}$M; 5.14×10$^{-4}$M, respectively). The molar ratio of —SH to protein was 7.8.

A solution of maleimidocaproyl hydrazone of adriamycin in DMF (5 mg/mL, 32.6 mL) was added to the antibody solution with gentle stirring and then incubated at 4° C. for 24 hrs. The solution was filtered through a 0.22µ cellulose acetate filter and then transferred to two dialysis tubes and dialyzed as described above. After dialysis, the contents of the tubes were combined, filtered and shaken with Bio-Beads™ SM-2 (Bio-Rad Laboratories, Richmond, Calif. 94804) for 24 hrs at 4° C. The beads were filtered off using a cellulose acetate filter to yield the conjugate solution. The concentration of protein and adriamycin were determined (8.66 mg/mL, 5.42×10$^{-5}$M; 168 µg/mL, 2.89×10$^{-4}$M, respectively). The protein yield is 97%. The molar ratio of adriamycin to protein is 5.33; and, unconjugated adriamycin is 0.5%.

EXAMPLE 8

General Procedure for Conjugating the Maleimidocaproyl-hydrazone of Adriamycin to a Relaxed Antibody 1. A solution (300 mL) of antibody (3 g, 10 mg/mL) in PBS buffer (note 1) is continuously blanketed with nitrogen, immersed in a 37° C. water bath and stirred gently with a magnetic stirrer. The solution is treated with 7 molar equivalents of DTT (notes 2,3) for 3 hrs. The —SH group molar ratio ("MR") to protein is determined initially and hourly and, for a maximally conjugated product, should remain constant at about 14 (notes 2,4).

2. The solution is transferred as quickly as possible to an Amicon diafiltration cell (Amicon, Division of W. R. Grace and Co., Beverly, Mass. 01915) (note 5) maintained at about 4° C. to about 7° C. The system is pressurized with argon or nitrogen and diafiltration is started using PBS buffer containing 0.1M histidine which had been precooled to about 4° C. to about 7° C.). The initial temperature of the effluent, immediately after starting the diafiltration, is 16°–18° C. and drops to 8°–9° C. within about 90 minutes. The effluent is monitored for a MR of —SH to protein and, when this value is <1, the diafiltration is complete (note 6).

3. The solution is transferred back to a round bottom flask equipped with a magnetic stirrer and kept in ice. The solution continuously is blanketed by nitrogen. The volume of the solution is noted. Aliquots of 0.1 mL are taken out and diluted with PBS buffer to 1.0 mL to determine the amount of protein in mg/mL (and also the molar equivalent of protein and the molarity of the —SH groups (and hence the MR of the —SH to protein). A solution of maleimidocaproylhydrazone of adriamycin in distilled water (5 mg/mL, 6.3×10$^{-3}$M) is prepared (note 7, 8). The amount (in mL) of this solution needed for conjugation is determined by the formula:

$$\frac{\text{(molarity of }-SH\text{)} \times \text{(volume of protein solution)} \times 1.05}{6.3 \times 10^{-3}}$$

(note 9) and this amount is added slowly to the protein solution which is stirred gently. The solution is kept a 4° C. for 30 min.

4. A column of Bio-Beads™ SM-2, mesh 20–50 (Bio-Rad Laboratories, Richmond, Calif. 94804) is prepared (note 10) at 4° C. The red protein solution is filtered through a 0.22μ cellulose acetate filter, then passed through the column at a rate of 2.5 mL/min and the red effluent collected. Finally PBS-0.1M histidine buffer is poured on top of the column and the effluent collected until it is colorless. The volume of the collected red solution is noted. An aliquot of 0.1 mL is diluted to 1 mL with PBS buffer and the amount of protein and adriamycin is measured. The amount of conjugated adriamycin is determined by absorbance at 495 nm ($\epsilon=8030$ cm$^{-1}$M$^{-1}$) and expressed in micromoles and micrograms per mL. The amount of protein, expressed in mg per mL and micromoles, is determined as above by reading the absorbance at 280 nm with a correction for the absorbance of adriamycin at the same wavelength according to the general formula $$\text{Antibody (mg/ml)} = \frac{A_{280} - (0.724 \times A_{495})}{1.4}$$

where A is the observed absorbance at the noted wavelength. The MR of adriamycin to protein then is calculated.

5. An aliquot of 5 mL of conjugate is passed over an Econo-Pac™ 10 SM-2 column (a prepacked Bio-Beads™ SM-2 column (Bio-Rad Laboratories, Richmond, Calif. 94804), volume 10 mL, that has been washed and equilibrated with PBS-0.1M histidine buffer) in the manner described above. The amount of protein and conjugated adriamycin is determined and the MR determined. This value should be the same as that of the bulk of the solution (note 11).

6. The conjugate is frozen in liquid nitrogen and stored at –80° C. Aliquots can be taken for determining cytotoxicity, binding and presence of free adriamycin (note 12).

Notes for the General Procedure

1. The antibody concentration is usually 7–10 mg/mL (~$6.25 \times 10^{-5}$M), and is the preferred concentration. If the concentration is much higher the solution can be diluted with buffer. If the concentration is less than 10 mg/mL, it is used as is. The concentration is determined by UV absorption at 280 nm: 1 mg/mL=1.4 absorbance units.

2. The DTT used is from Boeringer Mannheim Biochemicals, Indianapolis, Ind. 46250, mp 42°–43°. DTT should be recrystallized (e.g. for example, from etherhexane) if questions of quality arise. The purity is determined by mp, NMR and —SH content. Sulfhydryl titration is carried out according to the Ellman method (*Anal. Biochem.* 94, 75–81, 1979) as follows: An aliquot of 0.1 mL is diluted to 1 mL with PBS and treated with 0.05 mL of reagent (a 50 nmolar solution of dithio-bis-(2-nitrobenzoic acid) ("DTNB") in 100 nmolar Na$_2$HPO$_4$; pH of 7.04). A blank of 1 mL PBS is treated with DTNB in the same manner. After 5 minutes the absorbance (A) of the sample and the blank is measured at 412 nm and the molar concentration of —SH ("MC$_{SH}$") is determined according to the following formula:

$$MC_{SH} = \frac{(A_{sample} - A_{blank}) \times 10}{1.415 \times 10^4}$$

3. The DTT can be added as a solid or a solution. Preferably, a freshly prepared 10 mm solution in buffer is used. For purposes of the reaction scale provided, 13.13 mL generally are used.

4. The MR of —SH to protein is determined by measuring the molar concentration of SH according to the Ellman method (see note 2) and dividing that concentration by the molar protein concentration. Should this value be less than 14 during the reaction an appropriate additional amount of DTT is added.

5. On a scale of 3 g/300 mL, two Amicon cells of 350 mL each are used, dividing the solution into two portions of 150 mL per cell.

6. On the reaction scale provided, the diafiltration usually takes 2–4 hrs. The duration will depend on factors such as the age of the membrane, rate of stirring of solution and pressure in cell.

7. The hydrazone is not very soluble in PBS and a precipitate is formed in a short while.

8. Brief applications of a sonicator will facilitate dissolution in distilled water. The resulting solution is stable.

9. This amount provides for a 5% excess of the hydrazone. The process described generally takes about 15–20 minutes.

10. The Bio-Beads™ are prepared for chromatography by swelling them in methanol for at least one hr., preferably overnight, washing them with distilled water and finally equilibrating them with PBS-0.1M histidine buffer. For 3 g of protein 100 g of beads are used to form a column of 2.5 cm×30 cm.

11. Because of the inherent error of the spectroscopic methods used, a variation of 1 MR unit is accepted to be a satisfactory result. Generally, however, the MR varies less than 0.5 MR units.

12. The values of free adriamycin in the conjugate are generally much less than 1%.

EXAMPLE 9

Conjugate of Relaxed Chimeric BR96 with Maleimidocaproyl Hydrazone of Adriamycin Chimeric BR96, prepared in the manner previously described, was diluted with 0.0095M PBS to a protein concentration of 10.49 mg/mL. This solution (500 mL) was heated to 37° C., under a nitrogen atmosphere, in a water bath. Dithiothreitol (26.2 mL, 10 mM) in PBS was added and the solution was stirred for 3 hrs at 37° C. The solution was divided equally between two Amicon Model 8400 stirred ultrafiltration cells each fitted with a YM 30 ultrafilter (MW cutoff 30,000, 76 mm diam.) and connected via a Model CDS10 concentration/dialysis selector to a Model RC800 mini-reservoir (Amicon, Division of W. R. Grace and Co., Beverly Mass. 01915-9843). Each reservoir contained 800 mL of 0.0095M PBS-0.1M L-histidine. The protein solutions were dialyzed until the concentration of free thiol in the filtrate was 63 μM. The molar ratio of —SH/protein in the retentate was determined to be 8.16. The retentate was transferred from the cells to a sterile container under nitrogen and a solution of maleimidocaproyl hydrazone of adriamycin (42.6 mL, 5 mg/mL in water) was added with stirring. The conjugate was incubated at 4° C. for 48 hrs after which it was filtered through a 0.22μ cellulose acetate membrane. A 2.5 cm×50 cm Bio-Rad Econocolumn was packed with a slurry of 100 g of BioBeads™ SM-2 (Bio-Rad Laboratories, Richmond Calif. 94804) in 0.00095M-0.1M L-histidine buffer. The beads had been prepared by washing in methanol, followed by water then several volumes of buffer. The filtered conjugate was percolated through this column at 2 mL/min. After chromatography the conjugate was filtered through a 0.22µ cellulose acetate membrane, frozen in liquid nitrogen and stored at −80° C. The conjugate obtained had a molar ratio of 6.77 Adriamycin to protein and was obtained in 95% yield from chimeric BR96.

EXAMPLE 10

Conjugate of Relaxed Murine Antibody L6 with Maleimidocaproyl Hydrazone of Adriamycin Murine antibody L6, prepared as defined earlier, was diluted with 0.0095M PBS to a protein concentration of 11.87 mg/mL. This solution (350 mL) was heated to 37° C., under a nitrogen atmosphere, in a water bath. Dithiothreitol (18.2 mL, 10 mM) in PBS was added and the solution was stirred for 3 hrs at 37° C. The solution was divided equally between two Amicon Model 8400 stirred ultrafiltration cells each fitted with a YM 30 ultrafilter (MW cutoff 30,000, 76 mm diam.) and connected via a Model CDS10 concentration/dialysis selector to a Model RC800 mini-reservoir (Amicon, Division of W. R. Grace and Co., Beverly Mass. 01915-9843). Each reservoir contained 800 mL of 0.0095M PBS-0.1M L-histidine. The protein solutions were dialyzed until concentration of free thiol in the filtrate was 14 µM. The molar ratio of —SH/protein in the retentate was determined to be 9.8. The retentate was transferred from the cells to a sterile container under nitrogen and a solution of maleimidocaproyl hydrazone of adriamycin (40.4 mL, 5 mg/mL in water) was added with stirring. The conjugate was incubated at 4° C. for 48 hrs after which it was filtered through a 0.22µ cellulose acetate membrane. A 2.5 cm×50 cm Bio-Rad Econocolumn was packed with a slurry of 100 g of BioBeads™ SM-2 (Bio-Rad Laboratories, Richmond Calif. 94804) in 0.00095M-0.1M L-histidine buffer. The beads had been prepared by washing in methanol, followed by water then several volumes of buffer. The filtered conjugate was percolated through this column at 2 mL/min. After chromatography the conjugate was filtered through a 0.22µ cellulose acetate membrane, frozen in liquid nitrogen and stored at −80° C. The conjugate obtained had a molar ratio of 7.39 Adriamycin to protein and was obtained in 100% yield from murine L6.

BIOLOGICAL ACTIVITY

Representative conjugates of the present invention were tested in both in vitro and in vivo systems to determine biological activity. In these tests, the potency of conjugates of cytotoxic drugs was determined by measuring the cytotoxicity of the conjugates against cells of human cancer origin. The following describes representative tests used and the results obtained. Throughout the data presented, the conjugates are referred to using the form ligand-drug-molar ratio of ligand to drug. Thus, for example, "BR64-ADM-5.33", refers to a conjugate between antibody BR64 and adriamycin and the mole ratio of drug to antibody is 5.33. One skilled in the art will recognize that any tumor line expressing the desired antigen could be used in substitution of the specific tumor lines used in the following analyses.

TEST I

In vitro Activity of BR64-Adriamycin Conjugates

Figure 3:
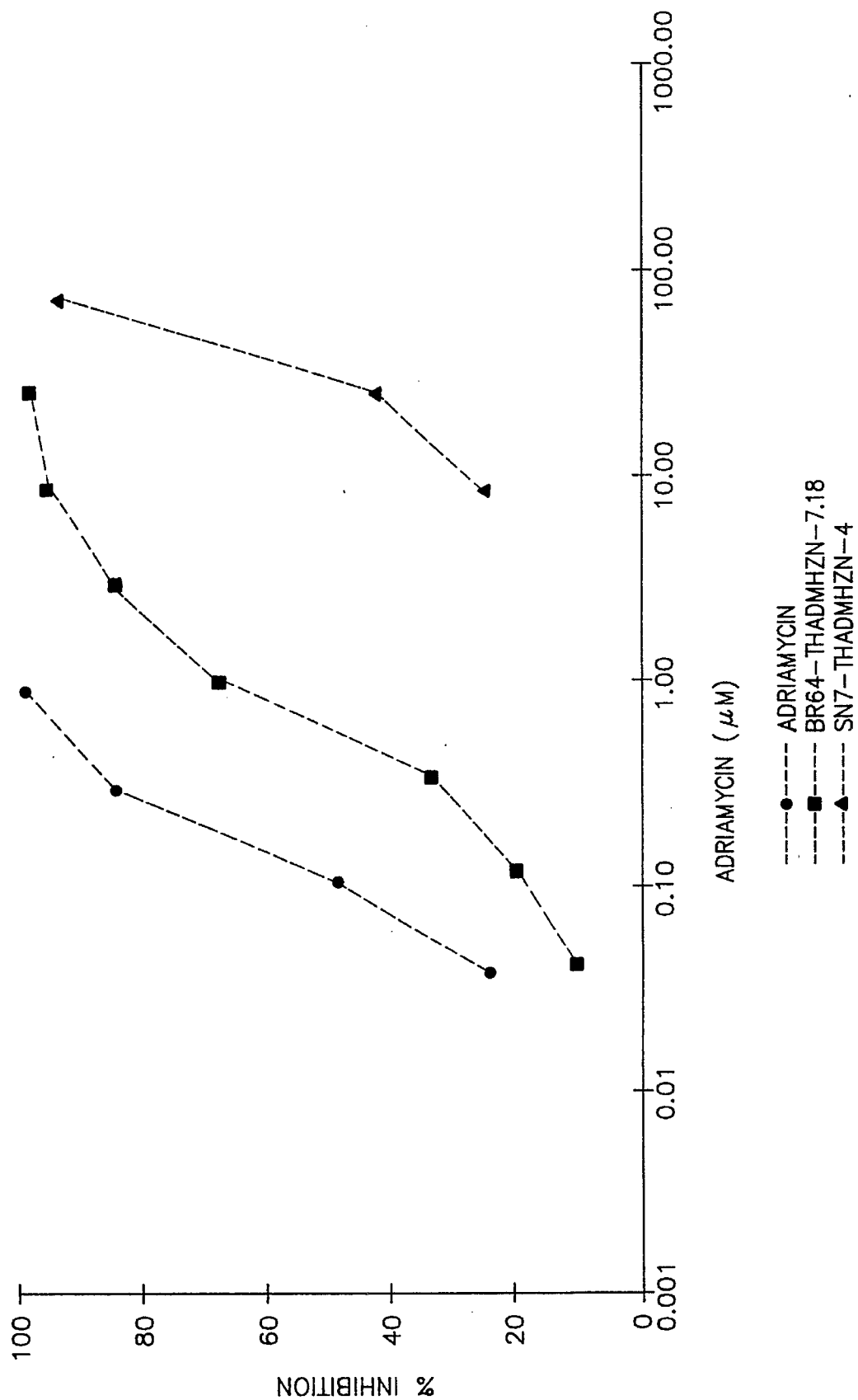
FIG. 3 provides in vitro cytotoxic activity data for BR64-Adriamycin conjugates of the invention against L2987 tumors.

The immunoconjugates of Examples 1B and 2 were tested in vitro against a human lung carcinoma line, L2987 [obtained from I. Hellström, Bristol-Myers Squibb Seattle; See also I. Hellström, et al., *Cancer Research* 50:2183 (1990)], which expresses the antigens recognized by monoclonal antibodies BR64, L6 and BR96. Monolayer cultures of L2987 cells were harvested using trypsin-EDTA (GIBCO, Grand Island, N.Y.), and the cells counted and resuspended to 1×10⁵/mL in RPMI-1640 containing 10% heat inactivated fetal calf serum ("RPMI-10% FCS"). Cells (0.1 mL/well) were added to each well of 96-well flat bottom microtiter plates and incubated overnight at 37° C. in a humidified atmosphere of 5% $CO_2$. Media was removed from the plates and serial dilutions of adriamycin or the antibody conjugates of adriamycin were added to the wells. All dilutions were performed in quadruplicate. Following a 2 hr drug or conjugate exposure, the plates were centrifuged (100×g, 5 min), the drug or conjugate removed, and the plates washed three times with RPMI-10% FCS. The cells were cultured in RPMI-10% FCS for an additional 48 hours. At this time the cells were pulsed for 2 hour with 1.0 µCi/well of ³H-thymidine (New England Nuclear, Boston, Mass.). The plates were harvested and the counts per minute ("CPM") determined. Inhibition of proliferation was determined by comparing the mean CPM for treated samples with that of the untreated controls. The data presented in FIG. 3 demonstrates the cytotoxicity against L2987 lung cells of binding immunoconjugate (MR of adriamycin to BR64 equal to 7.18, designated "BR64-THADMHZN-7.18") compared to a non-binding immunoconjugate of SN7 and adriamycin (MR of adriamycin to SN7 equal to 4, designated "SN7-THADMHZN-4"). The BR64 conjugates prepared by the method described in Example 1B are active and demonstrate antigen-specific cytotoxicity in this in vitro screen.

TEST II

In Vivo Activity of BR64-Adriamycin Conjugates

The immunoconjugates of Examples 1B and 2 were evaluated in vivo for antigen-specific antitumor activity. Congenitally athymic female mice of BALB/c background (BALB/c nu/nu; Harlan Sprague-Dawley, Indianapolis, Ind.) were used in these studies. Mice were housed in Thoren caging units on sterile bedding with controlled temperature and humidity. Animals received sterile food and water ad libitum. The L2987 human lung tumor line, described above, was used in these studies. This line has been shown to maintain expression of the BR64, BR96 and L6 antigens following repeated passage in vivo. The tumor lines were maintained by serial passage in athymic mice as described previously (P. A. Trail, et al., in vivo 3:319–24 (1989)). Tumors were measured, using calipers, in 2 perpendicular directions at weekly or biweekly intervals.

Tumor volume was calculated according to the equation:

$$V (mm^3) = \frac{(L \times W^2)}{2}$$

in which

V=volume (mm³)

L=measurement of longest axis (mm)

W=measurement (mm) of axis perpendicular to L.

Figure 4:
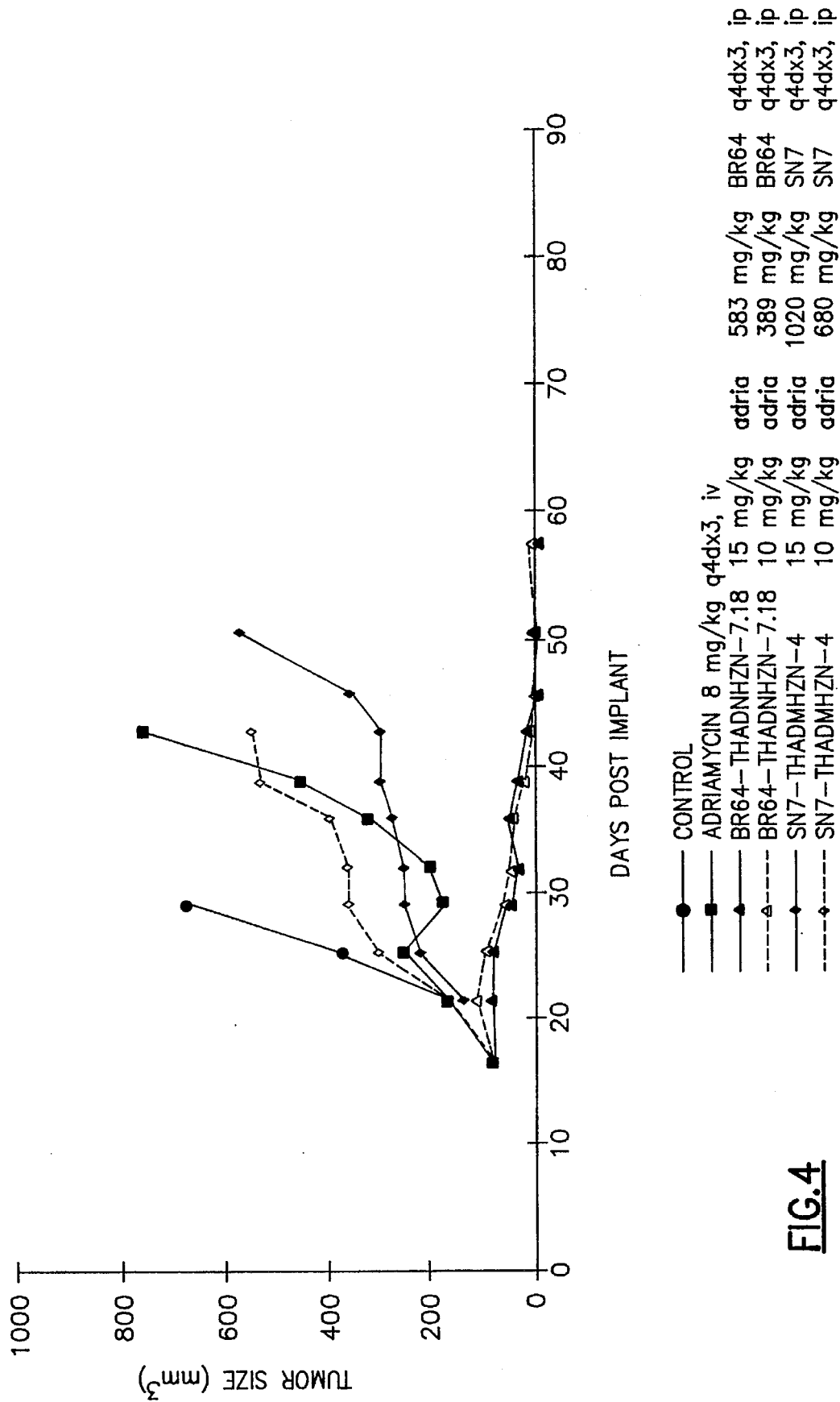
FIG. 4 provides in vivo cytotoxic activity data for BR64-Adriamycin conjugates of the invention against L2987 tumors.

Data are presented as the median tumor size for treated and control groups. Each treatment or control group contained 8–10 animals. Therapy was initiated when tumors had reached a median size of 50–100 mm³. Therapy was administered by the ip or iv route on various schedules as denoted. Adriamycin was diluted in normal saline and native antibody and adriamycin conjugates were diluted in phosphate buffered saline ("PBS") for administration. All dosages were administered on a weight basis (mg/kg) and were calculated for each animal. In these studies the antitumor activity of binding BR64 immunoconjugates was compared to that of optimized dosages of adriamycin, mixtures of native BR64 and adriamycin, and non-binding conjugates. Unconjugated adriamycin was administered according to the route, dosage, and schedule demonstrated to be optimal for the L2987 human xenograft model. The unconjugated adriamycin, therefore, was administered at a dose of 8 mg/kg by the iv route every fourth day for a total of 3 injections (denoted "8 mg/kg, q4d×3, iv"). The binding (BR64) and non-binding (SN7) immunoconjugates were administered at several doses by the ip route every fourth day for a total of 3 injections (denoted "q4d×3, ip"). As shown in FIG. 4 significant antitumor activity was observed following the administration of tolerated doses (10 and 15 mg/kg/injection) of the BR64-adriamycin conjugate. The antitumor activity observed following therapy with the BR64 conjugate was significantly better than that observed for therapy with optimized adriamycin and matching doses of a non-binding (SN7) conjugate.

In this experiment, complete tumor regressions were observed in 66% of the animals following treatment with 15 mg/kg/injection of the BR64 conjugate and 50% complete tumor regressions were observed following treatment with 10 mg/kg/injection of the BR64 conjugate. Partial or complete regressions of established L2987 tumors have not been observed following therapy with optimized adriamycin, mixtures of native BR64 and adriamycin, or equivalent doses of non-binding conjugates.

Figure 5A:
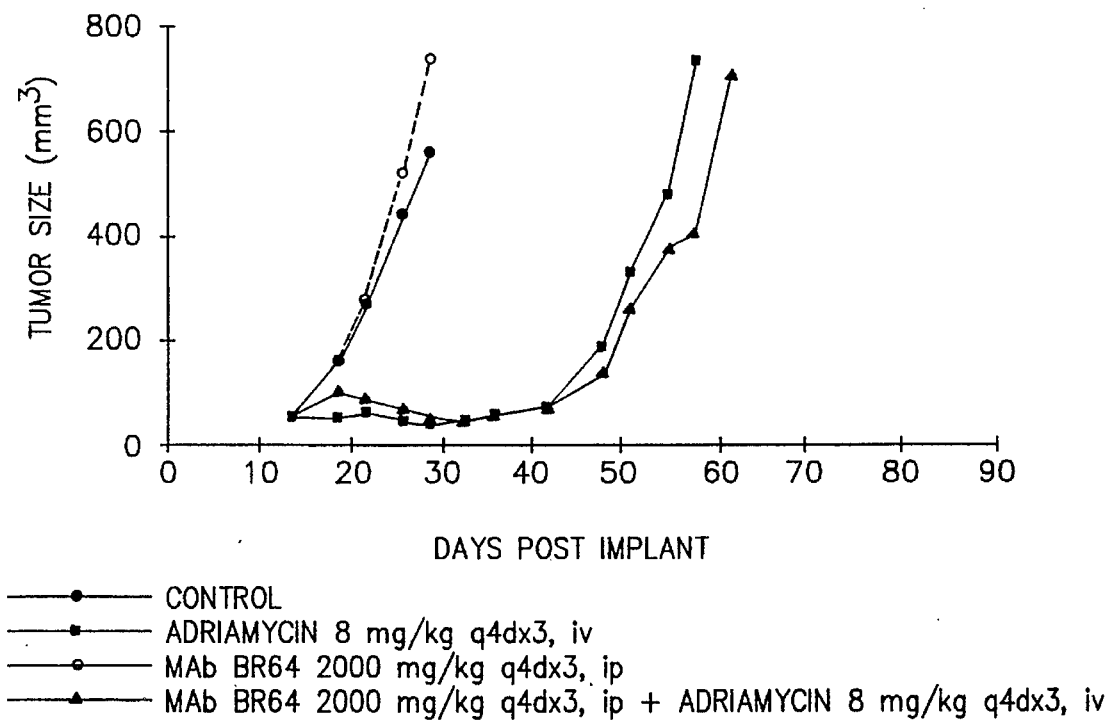
FIG. 5 provides comparative in vivo cytotoxic data for combination therapy using BR64, Adriamycin and a non-binding conjugate (SN7-Adriamycin).
Figure 5B:
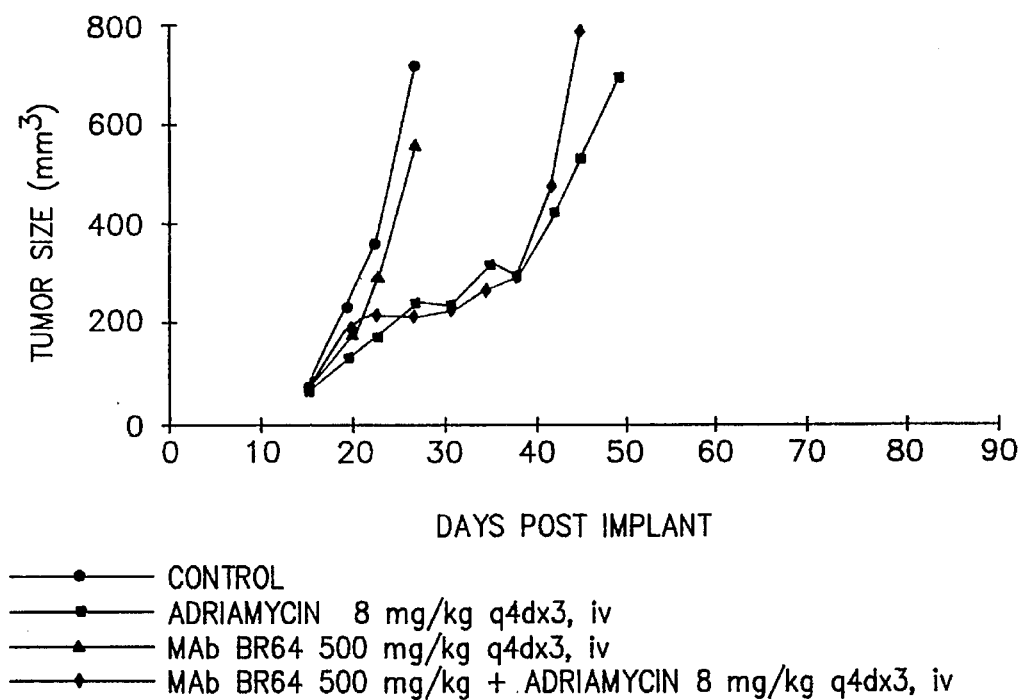
Figure 5C:
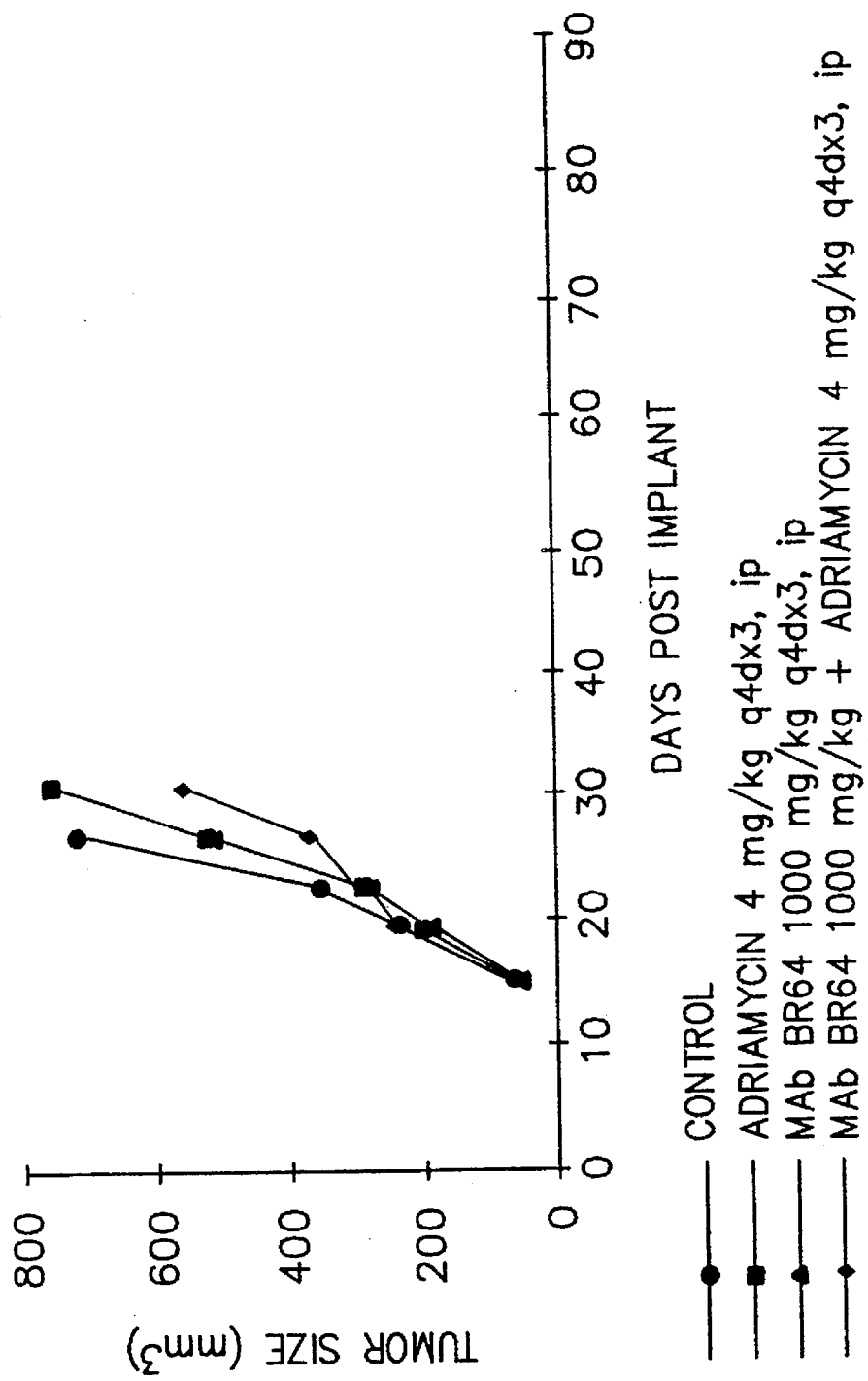

To demonstrate that the observed activity required the covalent coupling of the antibody to adriamycin, several control experiments using mixtures of native BR64 and adriamycin were performed. Representative data for several types of combined therapy are shown in FIGS. 5a–c. The antitumor activity observed for various modes of combined therapy with MAb and adriamycin was not significantly different from that observed for therapy with optimized adriamycin alone. Taken together these data indicate that the covalent coupling of BR64 to adriamycin is required to observe the antitumor activity described in FIG. 4.

TEST III
In Vivo Activity of Bombesin Conjugates

The conjugate of Example 4 was evaluated in vivo for antitumor activity. BALB/c athymic nude mice were implanted with H345 human small cell lung carcinoma tumor pieces (obtained from Dr. D. Chan, University of Colorado Medical School, Colorado), subcutaneously, using trocars. Tumors were allowed to grow to 50–100 mm$^3$ before initiation of treatment. Mice were treated i.v. on 23, 26, 28, and 30 days post-implant with adriamycin alone (1.6 mg/kg), or the conjugates bombesin-adrimycin ("BN-ADM(TH)", in an amount equivalent to 1.6 mg/kg adriamycin) or P77-adriamycin conjugate ("P77-ADM(TH)", in an amount equivalent to 1.6 mg/kg of adriamycin). P77 is a 12 amino acid peptide with an internal cysteine residue (sequence=KKLTCVQTRLKI) that does not bind to H345 cells and was conjugated to the maleimidocaproylhydrazone of adriamycin according to the procedure outlined in Example 4. Thus, the conjugate represents a non-binding conjugate with respect to H345 cells. Tumors were measured with calipers and tumor volume was calculated using formula:

$$V (mm^3) = \frac{(L \times W^2)}{2}$$

in which V, L, and W are as defined in Test II.

Figure 6:
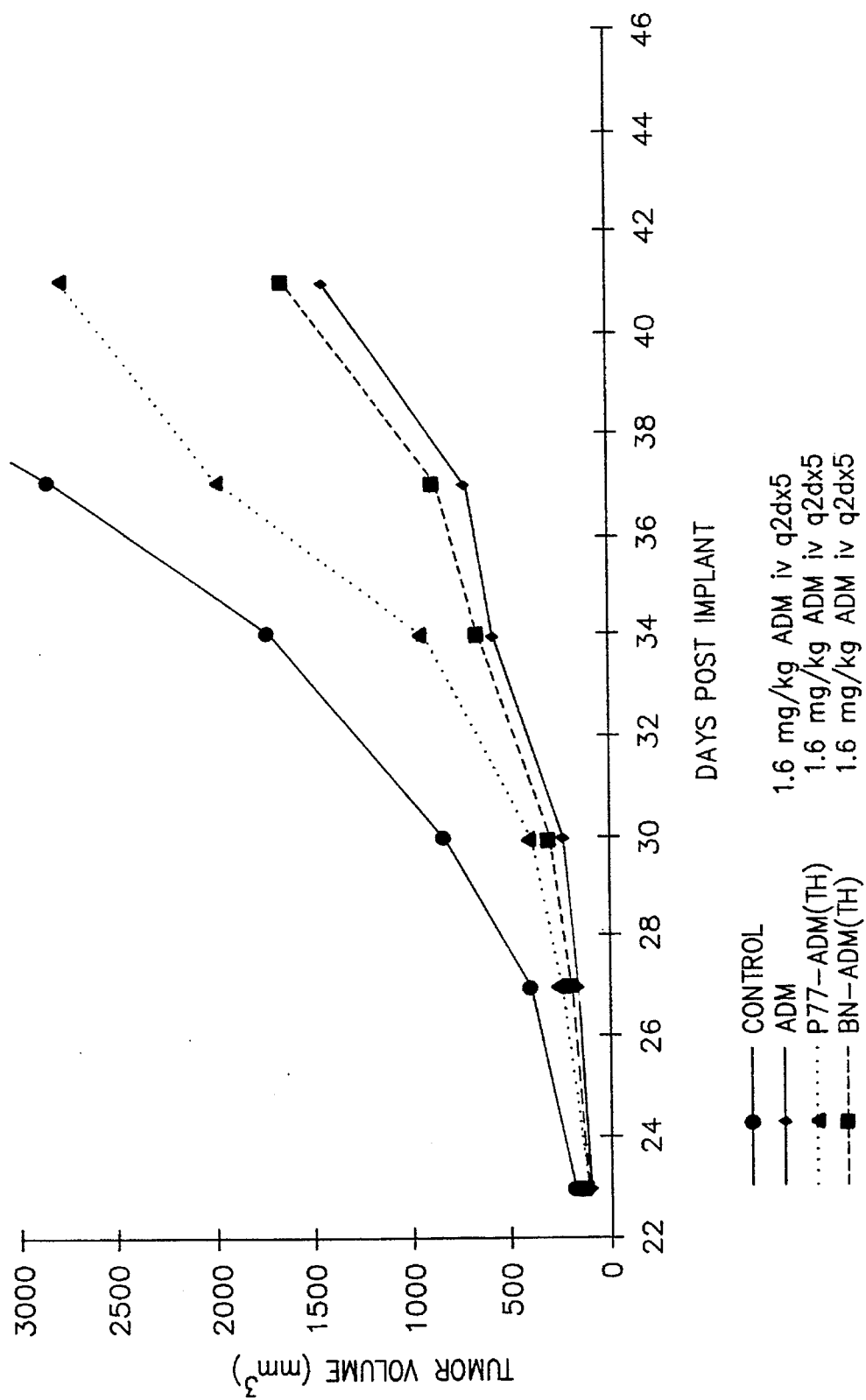
FIG. 6 provides in vivo cytotoxic activity data for Bombesin-Adriamycin conjugates of the invention against H345 tumors.

The median tumor volumes were determined and the observed results are shown in FIG. 6.

TEST IV
In Vitro Cytotoxicity Data for Relaxed ChiBR96 Antibody Conjugates

Figure 7:
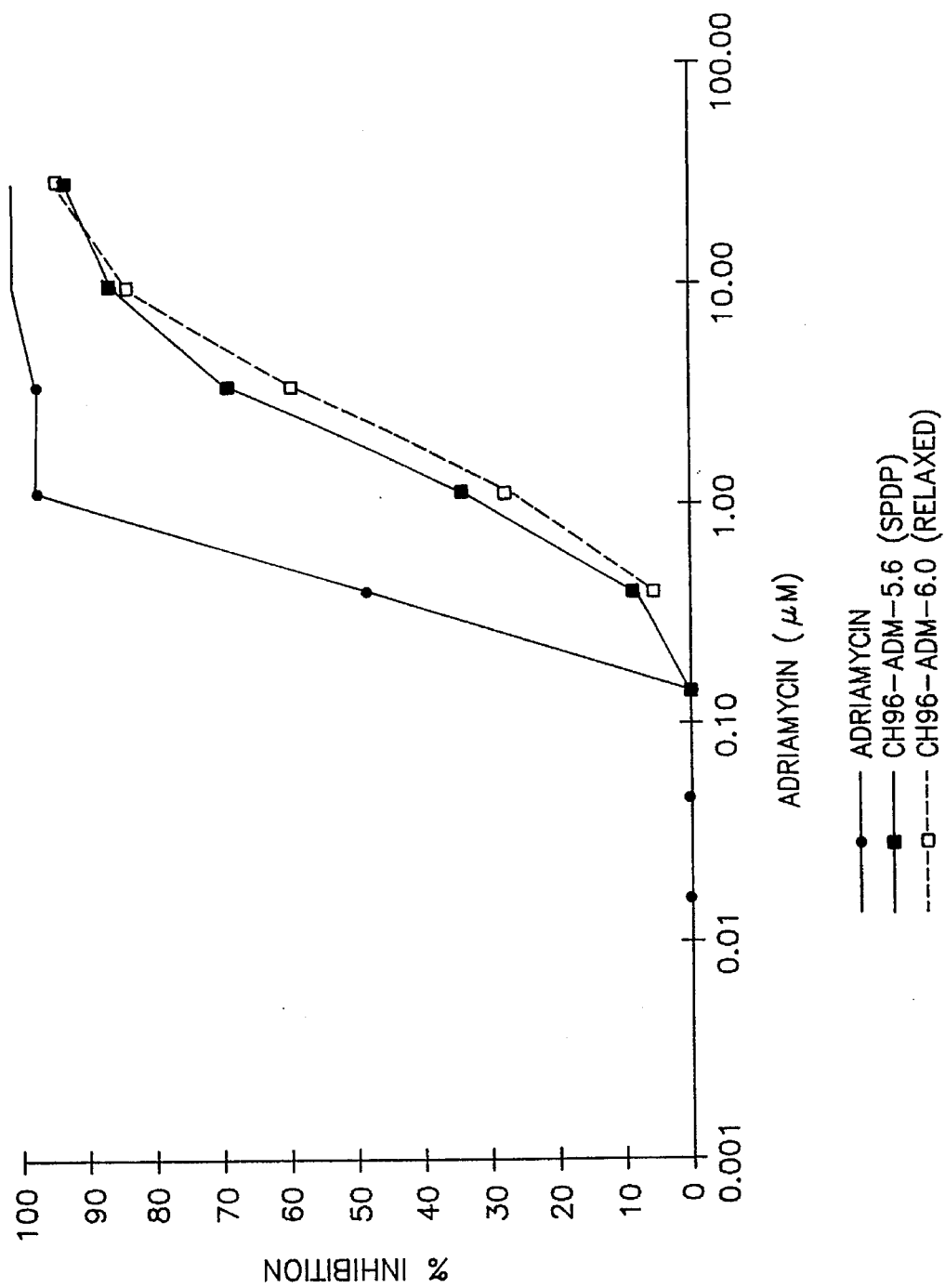
FIG. 7 provides in vitro cytotoxic activity data for Adriamycin conjugates of relaxed Chimeric BR96 and SPDP-thiolated Chimeric BR96.

Immunoconjugates of adriamycin and ChiBR96 antibody are prepared using the general method for preparing relaxed antibodies as described in Example 8. The conjugates were tested, using the protocol below, for in vitro cytotoxicity and their cytotoxicity was compared to that of free adriamycin, and SPDP-thiolated immunoconjugates prepared by the method described in Example 1B. The results of these tests are provided in FIG. 7.

Monolayer cultures of L2987 human lung cells were maintained in RPMI-1640 media containing 10% heat inactivated fetal calf serum (RPMI-10% FCS). The cells were harvested using trypsin-EDTA (GIBCO, Grand Island, N.Y.), and the cells counted and resuspended to 1×10$^5$/ml in RPMI-10% FCS. Cells (0.1 ml/well) were added to each well of 96 well microtiter plates and incubated overnight at 37° C. in a humidified atmosphere of 5% $CO_2$. Media was removed from the plates and serial dilutions of adriamycin or antibody/ADM conjugates added to the wells. All dilutions were performed in quadruplicate. Following a 2 hr drug or conjugate exposure, the plates were centrifuged (200×g, 5 min), the drug or conjugate removed, and the plates washed 3× with RPMI-10% FCS. The cells were cultured in RPMI-10% FCS for an additional 48 hr. At this time the cells were pulsed for 2 hr with 1.0 μCi/well of $^3$H-thymidine (New England Nuclear, Boston, Mass.). The plates were harvested and the counts per minute ("CPM") were determined. Inhibition of proliferation was determined by comparing the mean CPM for treated samples with that of the untreated control. IC$_{50}$ values are reported as μM of equivalent adriamycin.

TEST V
In Vivo Antitumor Activity of BR64 and Murine L6 Conjugates

The in vivo antitumor activity of immunoconjugates of adriamycin and relaxed BR64 or relaxed L6 was evaluated. The observed data are provided in FIG. 8.

Congenitally athymic female mice of BALB/c background (BALB/c nu/nu; Harlan Sprague-Dawley, Indianapolis, Ind.) were used. Mice were housed in Thoren caging units on sterile bedding with controlled temperature and humidity. Animals received sterile food and water ad libitum.

The L2987 human tumor line was established as tumor xenograft models in athymic mice. The tumor line was maintained by serial passage in vivo. Tumors were measured in 2 perpendicular directions at weekly or biweekly intervals using calipers. Tumor volume was calculated according to the equation:

$$V (mm^3) = \frac{L \times W^2}{2}$$

in which:

V=volume (mm$^3$)

L=measurement of longest axis (mm)

W=measurement of axis perpendicular to L

In general, there were 8–10 mice per control or treatment group. Data are presented as median tumor size for control or treated groups. Antitumor activity is expressed in terms of gross log cell kill ("LCK)" where:

$$LCK = \frac{T - C}{3.3 \times TVDT}$$

T-C is defined as the median time (days) for treated tumors to reach target size minus the median time for control tumors to reach target size and TVDT is the time (days) for control tumors to double in volume (250–500 mm$^3$). Partial tumor regression ("PR") refers to a decrease in tumor volume to ≦50% of the initial tumor volume; complete tumor regression ("CR") refers to a tumor which for a period of time is not palpable; and cure is defined as an established tumor which is not palpable for a period of time $\geq 10$ TVDTs.

For animals bearing the L2987 human lung tumor, therapy was typically initiated when the median tumor size was 75 mm$^3$ (12–14 days after tumor implant). The average TVDT was 4.8±0.9 days and antitumor activity was assessed at a tumor size of 500 mm$^3$. In several experiments (described below in Test VI) therapy was initiated when L2987 tumors were 225 mm$^3$ in size.

Materials under investigation were administered by the ip or iv route. Adriamycin was diluted in normal saline; antibody and antibody/adriamycin conjugates were diluted in phosphate buffered saline. Compounds were administered on a mg/kg basis calculated for each animal, and doses are presented as mg/kg of equivalent adriamycin/injection. Immunoconjugates were administered on a q4d×3 schedule. The maximum tolerated dose ("MTD") for a treatment regimen is defined as the highest dose on a given schedule which resulted in $\leq 20\%$ lethality.

Figure 8:
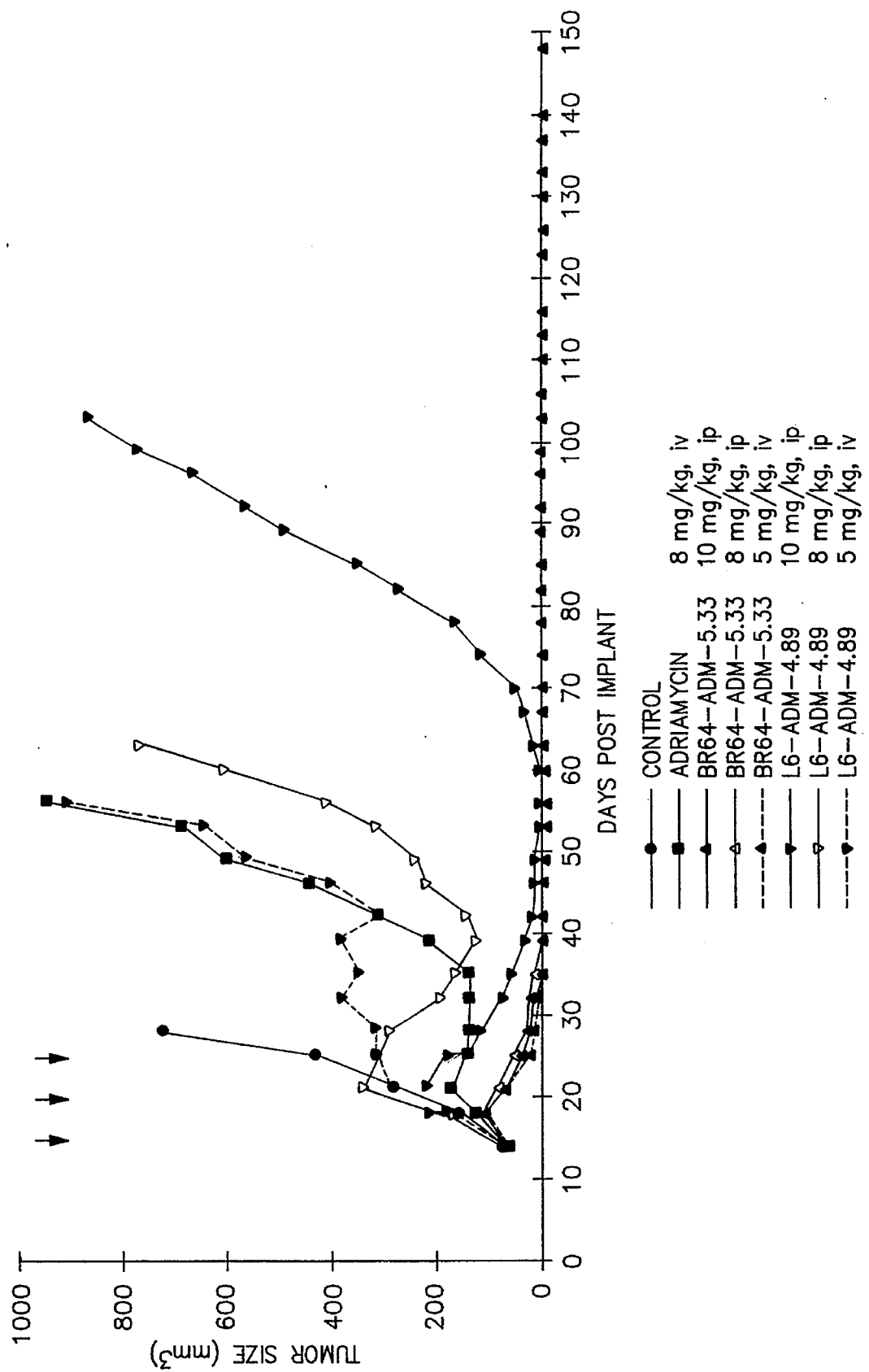
FIG. 8 provides in vivo cytotoxic activity data for Adriamycin conjugates of relaxed BR64 and relaxed chimeric L6 against L2987 tumors.

In the data shown in FIG. 8, injection of optimized doses of adriamycin produced antitumor activity equivalent to 1.1 LCK and tumor regressions were not observed. The BR64-ADM conjugate produced antitumor activity equivalent to >10 LCK at all doses tested and 89%, 78%, and 100% cures were observed at doses of 5 mg/kg, 8 mg/kg, and 10 mg/kg of BR64-ADM, respectively. At doses of 8 mg/kg or 10 mg/kg the L6-ADM conjugate produced antitumor activity (1.8 and 3.5 LCK, respectively) which was significantly better than that of optimized adriamycin but less than that of equivalent doses of internalizing BR64-ADM conjugates. Thus, the data show that the antitumor activity of binding non-internalizing L6-ADM conjugates is superior to that of unconjugated adriamycin. Treatment with L6-adriamycin conjugate results in lower antitumor activity than is observed with matching doses of the internalizing BR64-adriamycin conjugate.

TEST VI
In Vivo Antitumor Activity of ChiBR96-ADM Conjugates

The antitumor activity of ChiBR96-ADM conjugates was evaluated against established human lung ("L2987"), breast ("MCF7", obtainable from the ATCC under the accession number ATCC HTB 22; See also I. Hellström, et al., *Cancer Research* 50:2183 (1990)), and colon ("RCA" from M. Brattain, Baylor University; See also I. Hellström, et al., *Cancer Research* 50:2183 (1990)) tumors.

Animals were maintained and tumor xenograft models were established for the MCF7 and RCA and the L2987 human tumor lines as described for the L2987 in Test V. Materials were administered as described in Test V.

For animals bearing the L2987 human lung tumor, therapy typically was initiated when the median tumor size was 75 mm$^3$ (12–14 days after tumor implant). The average TVDT was 4.8±0.9 days and antitumor activity was assessed at a tumor size of 500 mm$^3$. In several experiments therapy was initiated when L2987 tumors were 225 mm$^3$ in size.

The MCF7 tumor is an estrogen-dependent human breast tumor line. Athymic mice were implanted with 0.65 mg (65 day release rate) estradiol pellets (Innovative Research of America, Toledo, Ohio) on the day of tumor implant. Therapy was initiated when the median tumor size was 100 mm$^3$ (typically 13 days after tumor implant). The MCF7 tumor had an average TVDT of 6.4±2.0 days and antitumor activity was assessed at 500 mm$^3$.

For animals bearing the RCA colon tumor, therapy was initiated 15 days after tumor implant when the median tumor size was 75 mm$^3$. The average TVDT for RCA tumor xenografts was 9.5±1.5 days and antitumor activity was assessed at 400 mm$^3$. Data for the antitumor activity of optimized adriamycin in the L2987, MCF7, and RCA xenograft models is summarized in the following Tables and referenced Figures.

The antitumor activity of the ChiBR96-ADM conjugates was compared to that of optimized adriamycin and equivalent doses of non-binding (IgG) immunoconjugates. In each model, complete tumor regressions and/or cures of established tumors were observed following the administration of tolerated doses of ChiBR96-ADM conjugate.

Figure 9:
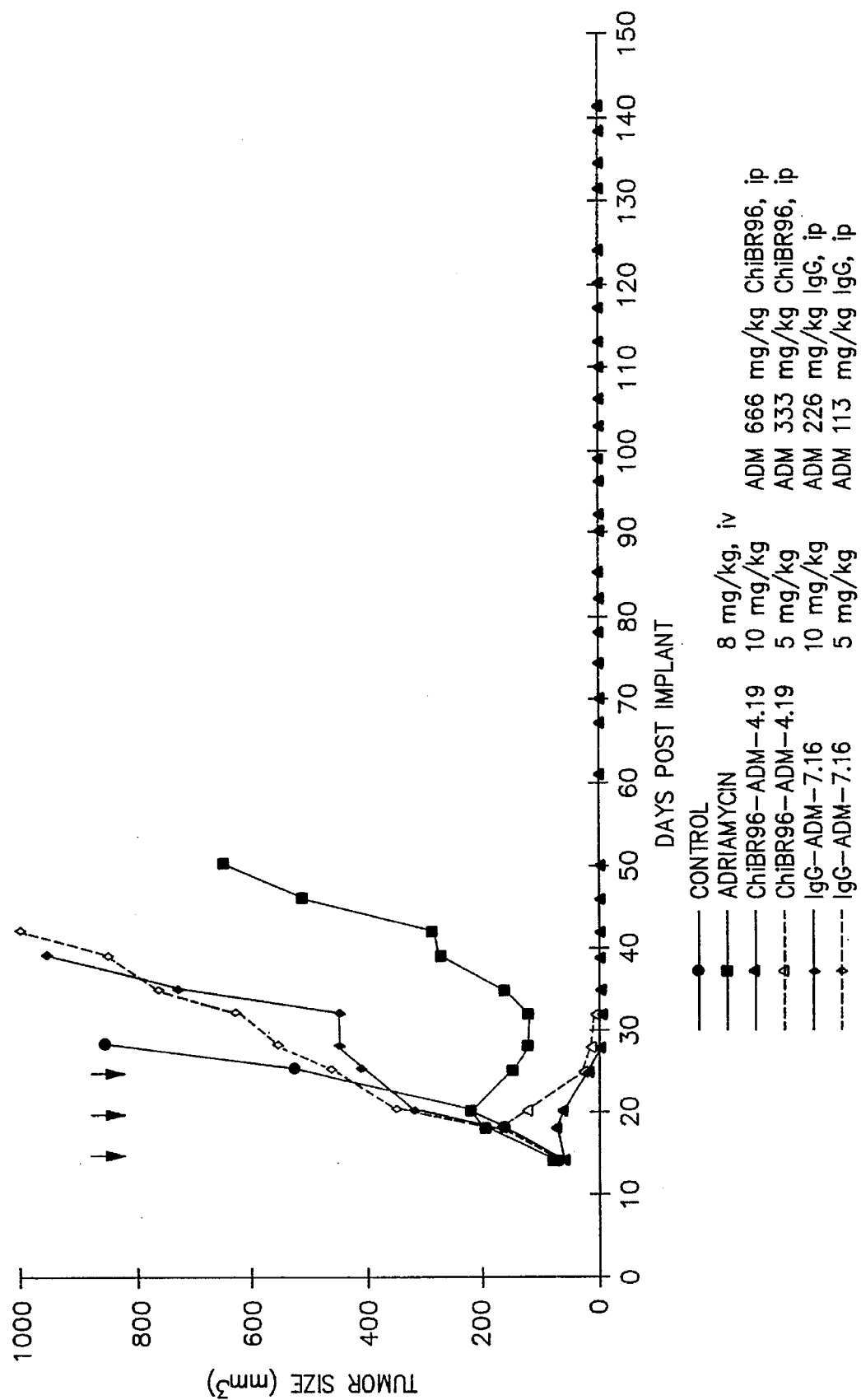
FIGS. 9 to 11 provide in vivo cytotoxic activity data against L2987 tumors for Adriamycin conjugates of relaxed Chimeric BR96 compared to free Adriamycin and non-binding conjugates.
Figure 10:
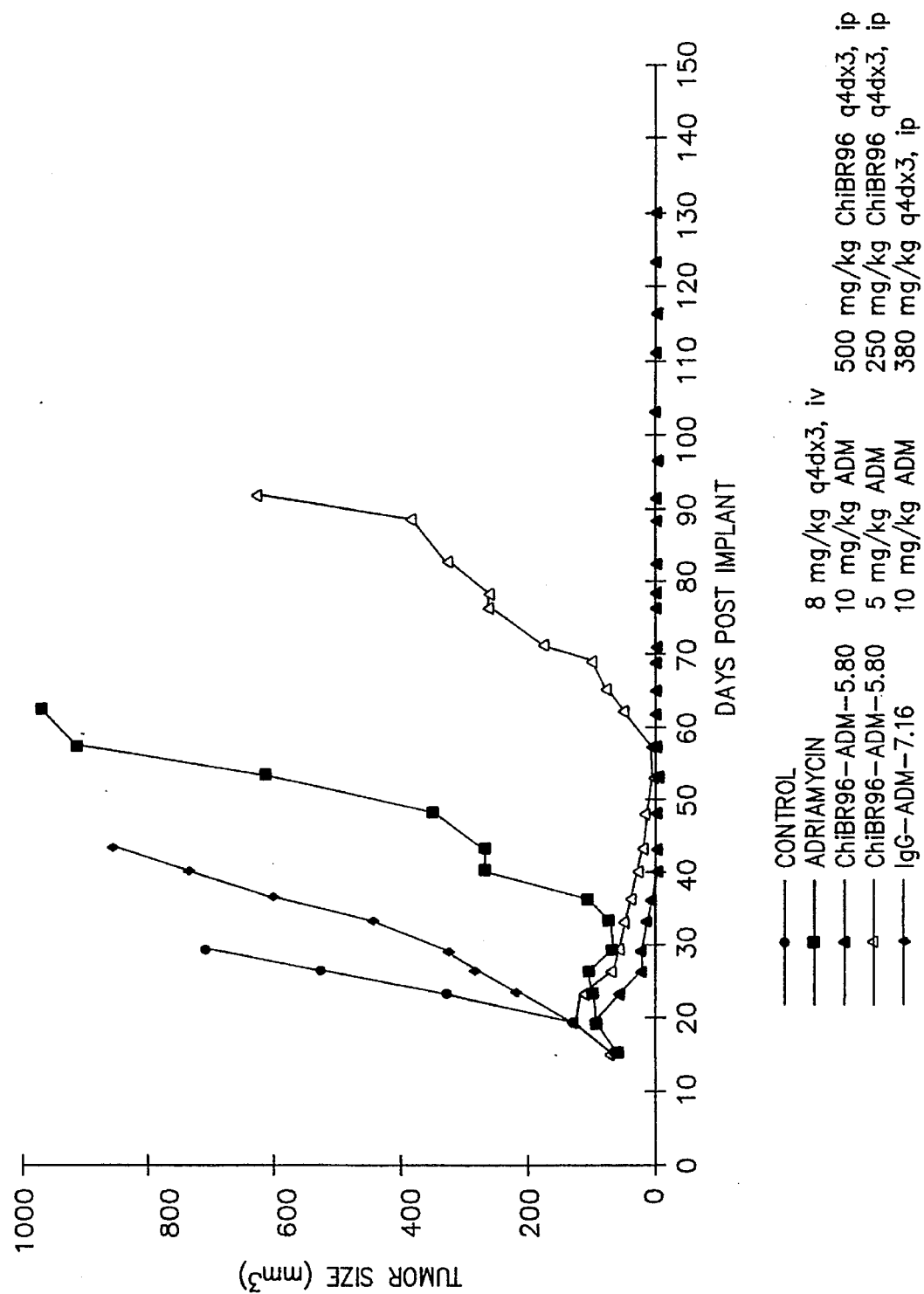

Representative data demonstrating the antigen-specific antitumor activity of ChiBR96-ADM conjugates is presented in FIGS. 9 and 10. As shown in FIG. 9, the ip administration of ChiBR96-ADM conjugate (MR=4.19) at a dose of 10 mg/kg equivalent of adriamycin produced antitumor activity equivalent to >10 LCK. At this dose of ChiBR96-ADM conjugate, 78% of the mice were cured of the tumor and an additional 11% of mice demonstrated a complete tumor regression. The administration of 5 mg/kg of the ChiBR96-ADM conjugate also produced antitumor activity equivalent to >10 LCK with 88% tumor cures and 12% complete tumor regressions. The antitumor activity observed following administration of ChiBR96-ADM conjugates (>10 LCK) was substantially better than that observed for optimized adriamycin (1.0 LCK). The ChiBR96-ADM conjugate was also more potent than optimized adriamycin; that is, the antitumor activity of the ChiBR96-ADM conjugate tested at a dose of 5 mg/kg equivalent adriamycin was superior to that of adriamycin tested at a dose of 8 mg/kg. The non-binding human IgG conjugate (MR=7.16) was not active against L2987 xenografts when tested at a dose of 10 mg/kg equivalent of adriamycin indicating that the superior activity of the ChiBR96-ADM conjugate was due to antigen specific binding of the immunoconjugate to L2987 tumor cells.

Similar data are presented in FIG. 10. As shown, the ChiBR96-ADM conjugate (MR=5.8) tested at a dose equivalent of 10 mg/kg adriamycin resulted in antitumor activity equivalent to >10 LCK. At this dose, 90% tumor cures and 10% complete tumor regressions were observed. The administration of 5 mg/kg of the ChiBR96-ADM conjugate resulted in 4.8 LCK with 10% cures, 50% complete and 10% partial tumor regressions. The antitumor activity of the ChiBR96-ADM conjugate greatly exceeded that of optimized adriamycin (1.6 LCK) and, as described above, the ChiBR96-ADM conjugate was more potent than unconjugated adriamycin. The non-binding IgG-ADM conjugate (MR=7.16) was not active at a dose of 10 mg/kg.

The antitumor activity of various preparation of ChiBR96-ADM conjugates prepared by the "relaxed" antibody technique and evaluated against established L2987 lung tumor xenograft is presented in Table II.

TABLE II

Antitumor Activity of ChiBR96-ADM Conjugates Against Established L2987 Human Lung Tumor Xenografts*

| Conjugate | Dose (mg/kg) ADM | Dose (mg/kg) Antibody | Route | LCK | % Tumor Regressions PR | % Tumor Regressions CR | % Tumor Regressions Cure | No. of Mice |
|---|---|---|---|---|---|---|---|---|
| ChiBR96-ADM-6.85 | 15 | 615 | ip | >10 | 10 | 0 | 80 | 10 |
|  | 10 | 410 | ip | >10 | 0 | 0 | 89 | 9 |
|  | 8 | 328 | iv | >10 | 0 | 0 | 100 | 9 |
|  | 5 | 205 | iv | >10 | 0 | 22 | 78 | 9 |
| ChiBR96-ADM-4.19 | 15 | 980 | ip | >10 | 0 | 11 | 89 | 9 |
|  | 10 | 654 | ip | >10 | 11 | 11 | 66 | 9 |
|  | 5 | 327 | iv | >10 | 0 | 11 | 89 | 9 |
|  | 2.5 | 164 | iv | >10 | 0 | 22 | 78 | 9 |
| ChiBR96-ADM-6.85 | 10 | 410 | ip | >10 | 11 | 11 | 78 | 9 |
|  | 8 | 328 | iv | >10 | 0 | 0 | 100 | 9 |
|  | 5 | 205 | iv | >10 | 0 | 11 | 89 | 9 |
| ChiBR96-ADM-4.19 | 10 | 654 | ip | >10 | 0 | 0 | 100 | 9 |
|  | 5 | 327 | iv | >10 | 0 | 0 | 100 | 9 |
| ChiBR96-ADM-4.19 | 10 | 654 | ip | >8 | 0 | 22 | 78 | 9 |
|  | 5 | 327 | ip | >8 | 0 | 11 | 89 | 9 |
| ChiBR96-ADM-5.80 | 10 | 500 | ip | >10 | 0 | 10 | 90 | 10 |
|  | 5 | 250 | ip | >4.8 | 10 | 50 | 10 | 10 |
| ChiBR96-ADM-6.82 | 5 | 204 | iv | >10 | 22 | 22 | 55 | 9 |
|  | 2 | 82 | iv | 3.5 | 44 | 33 | 0 | 9 |
|  | 1 | 41 | iv | 2.0 | 0 | 22 | 0 | 9 |
| ChiBR96-ADM-6.82 | 10 | 400 | ip | >5.3 | 11 | 11 | 56 | 9 |
|  | 5 | 200 | ip | 4.8 | 30 | 10 | 40 | 10 |
|  | 2.5 | 100 | ip | 2.9 | 30 | 0 | 30 | 10 |
|  | 1.25 | 50 | ip | 1.1 | 11 | 0 | 11 | 9 |
|  | 0.62 | 25 | ip | 0 | 0 | 0 | 0 | 9 |
|  | 5 | 200 | iv | >5.3 | 10 | 20 | 70 | 10 |
|  | 2.5 | 100 | iv | 2.9 | 22 | 33 | 0 | 9 |
|  | 1.25 | 50 | iv | 1.5 | 11 | 11 | 0 | 9 |
|  | 0.62 | 25 | iv | 0.6 | 0 | 0 | 0 | 9 |
| Adriamycin | 8 | — | iv | 1–1.8 | 3.6 | 0 | 0 | 55 |

*All treatment administered on a q4dx3 schedule

As shown, the antitumor activity of ChiBR96-ADM conjugates is superior to that of optimized adriamycin and the ChiBR96-ADM conjugates are 6–8 fold more potent than unconjugated adriamycin.

Figure 11:
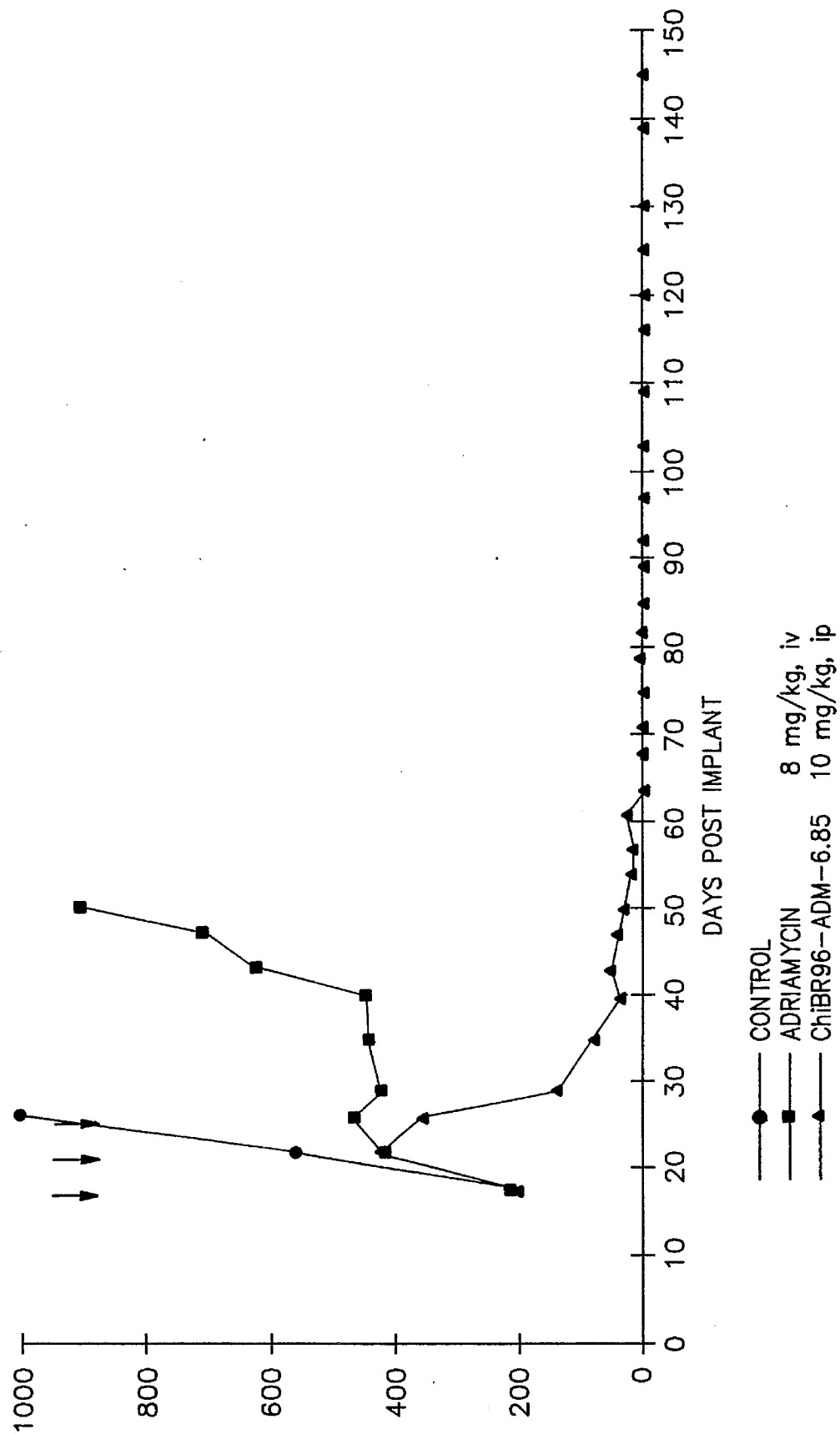

The antitumor activity of ChiBR96-ADM conjugates was also evaluated against large (225 mm$^3$) established L2987 tumors (FIG. 11). The administration of the ChiBR96-ADM conjugate (MR=6.85) at a dose of 10 mg/kg equivalent adriamycin resulted in antitumor activity equivalent to >10 LCK and 70% cures and 30% partial tumor regressions were observed.

The antitumor activity of unconjugated ChiBR96 antibody was evaluated using established (50–100 mm$^3$) L2987 human lung tumor xenografts. As shown in Table III, ChiBR96 antibody administered at doses of 100, 200 or 400 mg/kg was not active against established L2987 tumors. The antitumor activity of mixtures of ChiBR96 and adriamycin was not different from that of adriamycin administered alone. Therefore, the antitumor activity of the ChiBR96-ADM conjugates reflects the efficacy of the conjugate itself rather than a synergistic antitumor effect of antibody and adriamycin.

TABLE III

Antitumor Activity of Adriamycin, ChiBR96, and Mixtures of ChiBR96 and Adriamycin Against Established L2987 Human Lung Tumor Xenografts

| Treatment | Dose (mg/kg)$^a$ ADM | Dose (mg/kg)$^a$ ChiBR96 | Log Cell Kill | % Tumor Regressions PR | % Tumor Regressions CR | % Tumor Regressions Cure | No. of Mice |
|---|---|---|---|---|---|---|---|
| Adriamycin | 8 | — | 1.5 | 0 | 0 | 0 | 9 |
| ChiBR96 | — | 400 | 0 | 0 | 0 | 0 | 8 |
|  | — | 200 | 0 | 0 | 0 | 0 | 8 |
|  | — | 100 | 0 | 0 | 0 | 0 | 8 |
| Adriamycin + ChiBR96 | 8 | 400 | 1.8 | 11 | 0 | 0 | 9 |
|  | 8 | 200 | 1.6 | 0 | 0 | 0 | 9 |
|  | 8 | 100 | 1.9 | 0 | 0 | 0 | 8 |

$^a$Treatment administered iv on a q4dx3 schedule

In summary ChiBR96-ADM conjugates demonstrated antigen-specific antitumor activity when evaluated against established L2987 human lung tumors. The antitumor activity of ChiBR96-ADM conjugates was superior to that of optimized adriamycin, mixtures of ChiBR96 and adriamycin, and equivalent doses of non-binding conjugates. The ChiBR96-ADM conjugates were approximately 6 fold more potent than unconjugated adriamycin. Cures or complete regressions of established tumors were observed in 50% of animals treated with doses of ≧2.5 mg/kg of ChiBR96-ADM conjugate.

Figure 12:
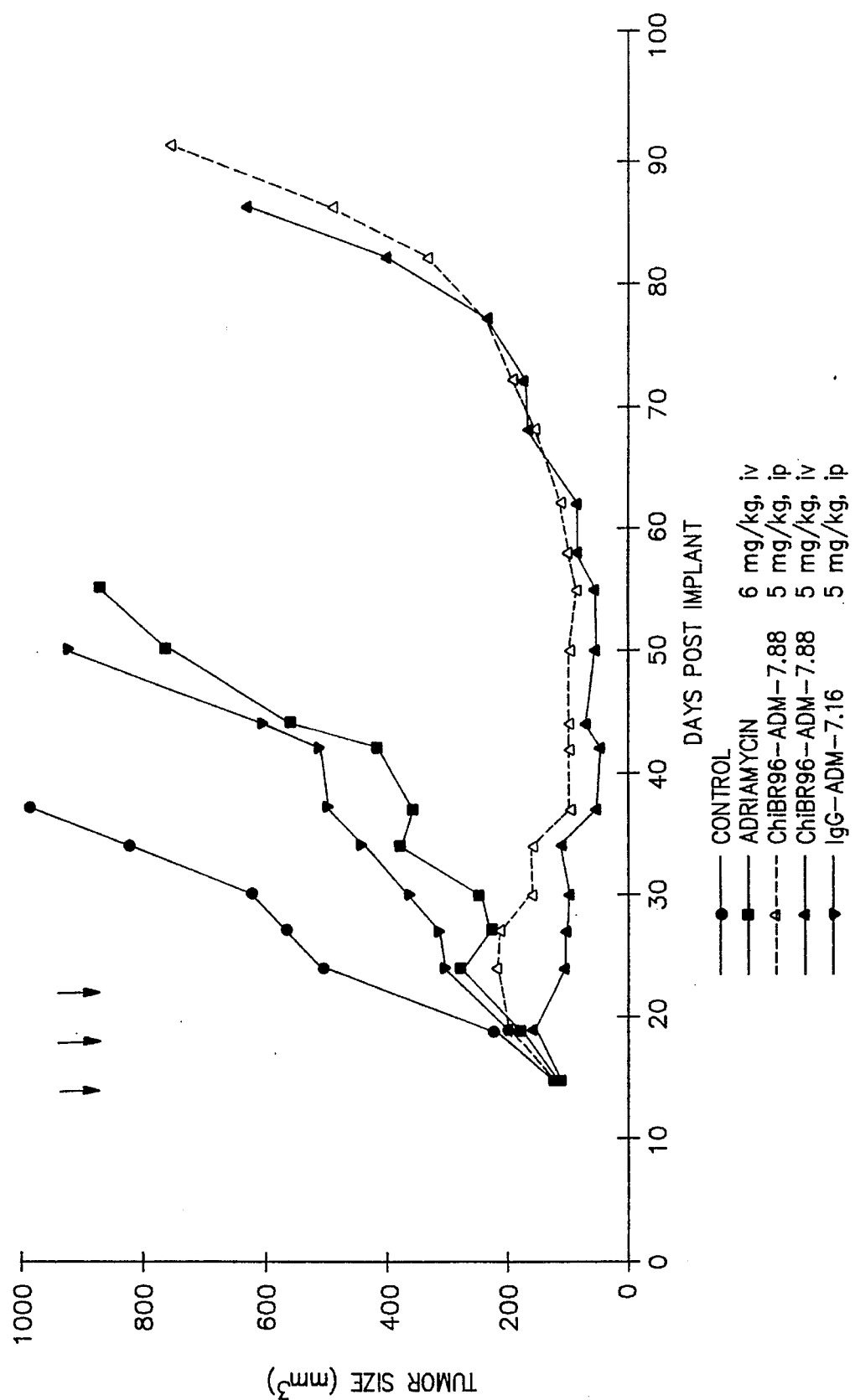
FIG. 12 provides in vivo cytotoxic activity data for Adriamycin conjugates of relaxed Chimeric BR96 against MCF7 Human Breast Tumors.

As shown in FIG. 12, ChiBR96-ADM conjugates (MR= 7.88) demonstrated antigen-specific antitumor activity against established (75–125 mm$^3$) MCF7 tumors. The activity of ChiBR96-ADM conjugate administered at a dose of 5 mg/kg by either the ip or iv route (4.2 LCK) was superior to that of optimized adriamycin (1.4 LCK) or equivalent doses of non-binding IgG conjugate (1.2 LCK). The antitumor activity of ChiBR96-ADM and non-binding IgG-ADM conjugates is summarized in Table IV. The MTD of ChiBR96-ADM conjugates like that of free adriamycin is lower in the MCF7 model due to the estradiol supplementation required for tumor growth.

TABLE IV

Summary of Antitumor Activity of ChiBR96-ADM Thioether Conjugates Evaluated Against Established MCF7 Human Breast Tumor Xenografts

| Conjugate | Dose (mg/kg)[a] | | Route | Log Cell Kill | % Tumor Regressions | | | No. of Mice |
|---|---|---|---|---|---|---|---|---|
| | ADM | ChiBR96 | | | PR | CR | Cures | |
| ChiBR96-ADM-7.88 | 10 | 350 | ip | —[b] | — | — | — | 10 |
| | 5 | 175 | ip | 4.2 | 30 | 0 | 0 | 10 |
| | 5 | 175 | iv | 4.2 | 50 | 10 | 0 | 10 |
| IgG-ADM-7.16 | 5 | 225 | ip | 1.1 | 0 | 0 | 0 | 10 |
| | 2.5 | 112 | ip | 0.6 | 0 | 0 | 0 | 10 |
| Adriamycin | 2.5 | 112 | iv | 0.8 | 0 | 0 | 0 | 10 |
| | 6 | 0 | iv | 1.4 | 0 | 0 | 0 | 10 |

Figure 13:
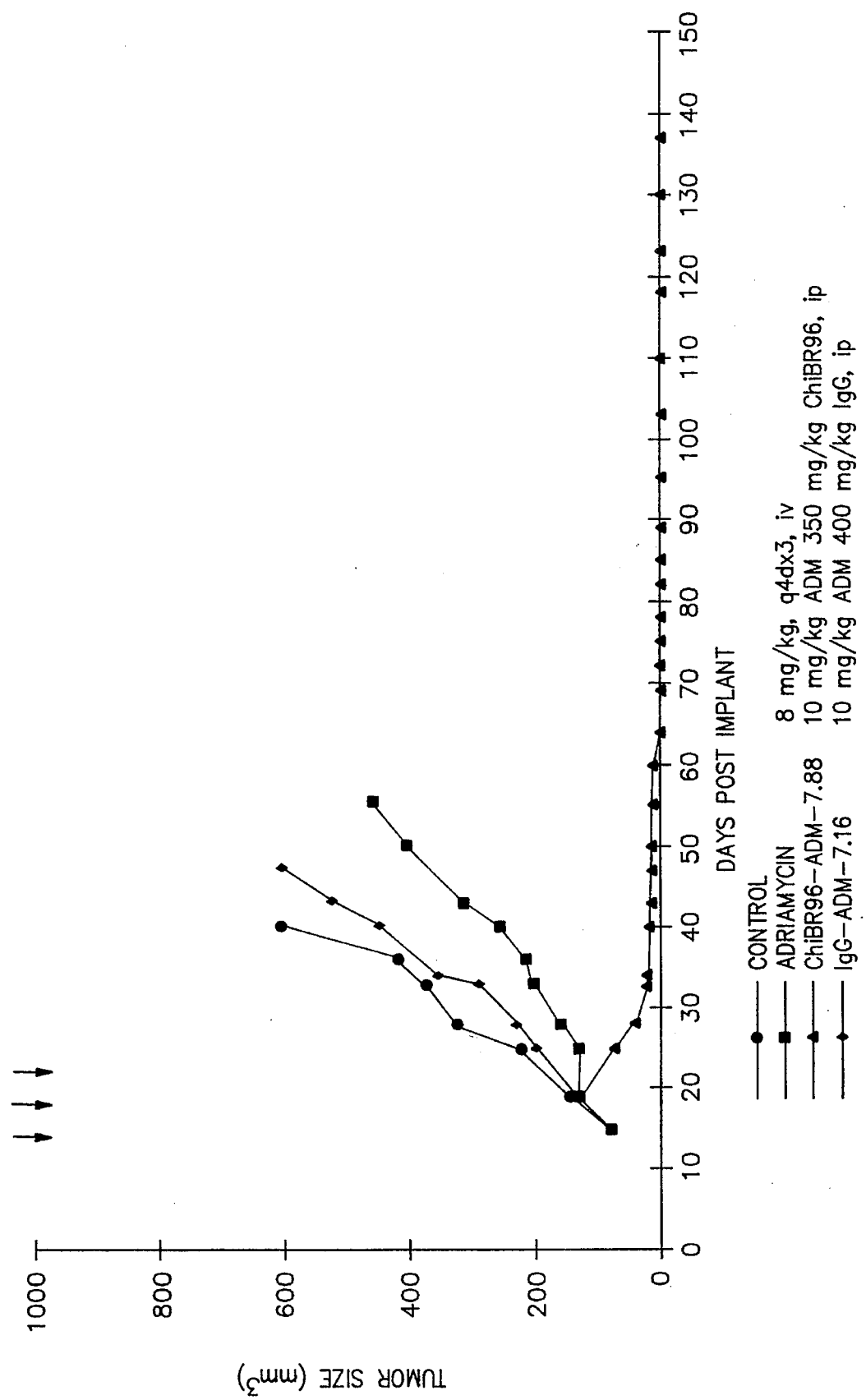
FIG. 13 provides in vivo cytotoxic activity data for Adriamycin conjugates of relaxed Chimeric BR96 against RCA Human Colon Tumors.

[a]All therapy administered q4dx3
[b]40% lethality occurred at this dose of immunoconjugate The antigen-specific antitumor activity and dose response of ChiBR96-ADM conjugates was also evaluated in the RCA human colon carcinoma model. RCA tumors are less senstive to unconjugated adriamycin than are L2987 and MCF7 tumors. In addition, as described previously, RCA tumors have a longer tumor volume doubling time than L2987 or MCF7 tumors, are more poorly vascularized, and the localization of radiolabelled BR64 antibody is lower in RCA tumors than in L2987 tumors. As shown in FIG. 13, the antitumor activity of the ChiBR96-ADM conjugate (MR=7.88) administered at a dose of 10 mg/kg was superior to that of adriamycin and an equivalent dose of non-binding IgG conjugate (MR=7.16). As shown in Table V, the ChiBR96-ADM conjugate tested at a dose of 10 mg/kg produced antitumor activity equivalent to >3 LCK. At this dose of ChiBR96-ADM conjugate, 89% cures and 11% partial tumor regressions occurred. In this experiment, unconjugated adriamycin showed antitumor activity, equivalent to 0.4 LCK. Thus, in this experiment, the BR96-ADM conjugate produced 89% cures of established tumors whereas unconjugated adriamycin was inactive.

In summary, the ChiBR96-ADM conjugate demonstrated antigen-specific antitumor activity in the RCA human colon tumor model. Cures and complete regressions of established RCA tumors were observed following the administration of ChiBR96-ADM conjugate at doses of 5–10 mg/kg.

The invention has been described with reference to specific examples, materials and data. As one skilled in the art will appreciate, alternate means for using or preparing the various aspects of the invention may be available. Such alternate means are to be construed as included within the intent and spirit of the present invention as defined by the following claims.

We claim:

1. A compound of Formula (I):

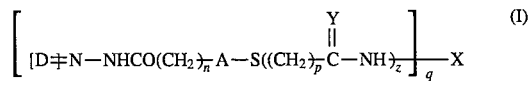

in which D is an anthracycline antibiotic;

n is an integer from 1 to 10;

p is an integer from 1 to 6;

Y is O or $NH_2^+Cl^-$;

a is 0 or 1;

q is about 1 to about 10;

X is a ligand that specifically binds with a target cell population; and

A is a succinimido moiety;

wherein the anthracycline antibiotic is bound through the 13-keto position of the anthracycline.

TABLE V

Summary of Antitumor Activity of ChiBR96-ADM Thioether Conjugates Evaluated Against Established RCA Human Colon Tumor Xenografts

| Conjugate | Dose (mg/kg)[a] | | Route | Log Cell Kill | % Tumor Regressions | | | No. of Mice |
|---|---|---|---|---|---|---|---|---|
| | ADM | ChiBR96 | | | PR | CR | Cures | |
| ChiBR96-ADM-7.88 | 10 | 350 | ip | >3 | 11 | 0 | 89 | 9 |
| | 5 | 175 | ip | 0.6 | 11 | 22 | 11 | 9 |
| | 2.5 | 85 | ip | 0.2 | 0 | 0 | 0 | 9 |
| | 2.5 | 85 | iv | 0.6 | 11 | 0 | 0 | 9 |
| IgG-ADM-7.16 | 10 | 405 | ip | 0 | 0 | 0 | 0 | 9 |
| Adriamycin | 8 | 0 | iv | 0.4 | 0 | 0 | 0 | 9 |

[a]All therapy administered q4dx3

2. An anthracycline antibiotic conjugate compound of Formula (Ia):

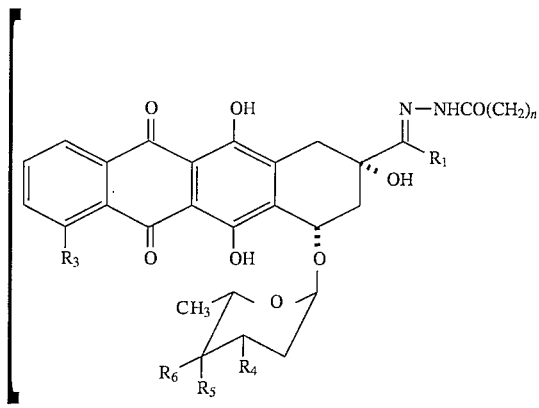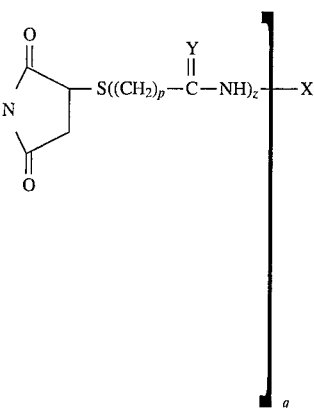

in which

R$_1$ is —CH$_3$, —CH$_2$OH, —CH$_2$OCO(CH$_2$)$_3$CH$_3$ or —CH$_2$OCOCH(C$_2$H$_5$)$_2$;

R$_3$ is —OCH$_3$, —OH or hydrogen;

R$_4$ is —NH$_2$, —NHCOCF$_3$, 4-morpholinyl, 3-cyano-4-morpholinyl, 1-piperidinyl, 4-methoxy-1-piperidinyl, benzylamine, dibenzylamine, cyanomethyl amine or 1-cyano-2-methoxyethyl amine;

R$_5$ is —OH, —OTHP or hydrogen;

R$_6$ is —OH or hydrogen, provided that R$_6$ is not —OH when R$_5$ is —OH or —OTHP;

n is an integer from 1 to 10;

p is an integer from 1 to 6;

Y is O or NH$_2^+$Cl$^{31}$;

z is 0 or 1;

q is about 1 to about 10; and

X is a ligand that specifically binds with a target cell population.

3. A compound of Formula (Ib):

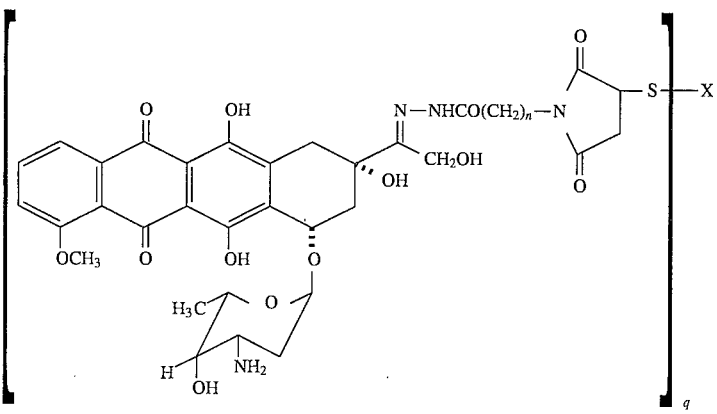

in which n is an integer from 1 to 10;

q is about 1 to about 10; and

X is a ligand that specifically binds with a target cell population.

4. A compound of Formula (Ic):

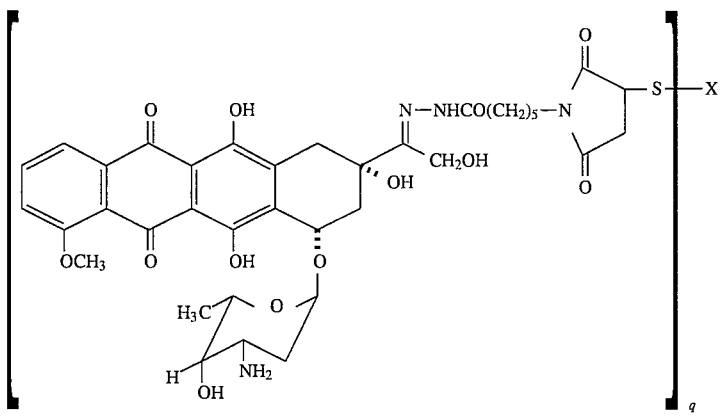

in which q is about 4 to about 8; and

X is a ligand that specifically binds with a target cell population.

5. A formulation which comprises as an active ingredient a compound of Formula (Ia):

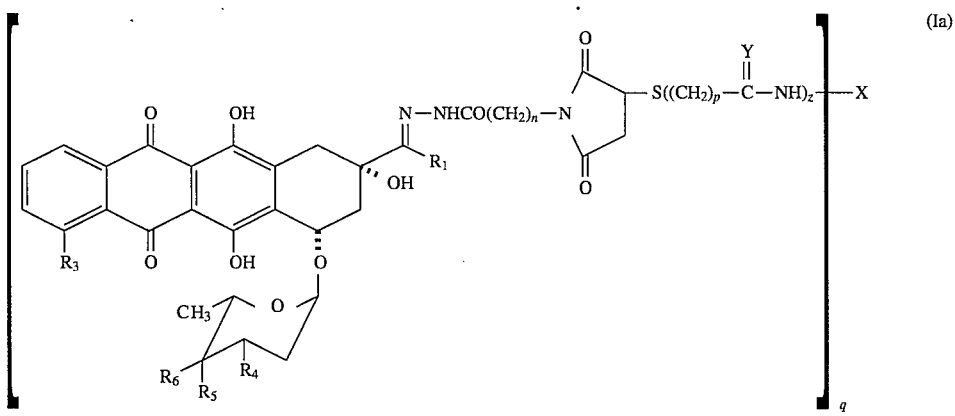

in which $R_1$ is —$CH_3$, —$CH_2OH$, —$CH_2OCO(CH_2)_3CH_3$ or —$CH_2OCOCH(C_2H_5)_2$;

$R_3$ is —$OCH_3$, —OH or hydrogen;

$R_4$ is —$NH_2$, —$NHCOCF_3$, 4-morpholinyl, 3-cyano-4-morpholinyl, 1-piperidinyl, 4-methoxy-1-piperidinyl, benzylamine, dibenzylamine, cyanomethyl amine or 1-cyano-2-methoxyethyl amine;

$R_5$ is —OH, —OTHP or hydrogen;

$R_6$ is —OH or hydrogen, provided that $R_6$ is not —OH when $R_5$ is —OH or —OTHP;

n is an integer from 1 to 10;

p is an integer from 1 to 6;

Y is O or $NH_2^+Cl^-$;

z is 0 or 1;

q is about 1 to about 10; and

X is a ligand that specifically binds with a target cell population;

in a pharmaceutically acceptable amount associated with a pharmaceutically acceptable carrier, diluent or excipient therefor.

6. A formulation which comprises as an active ingredient a compound of Formula (Ib):

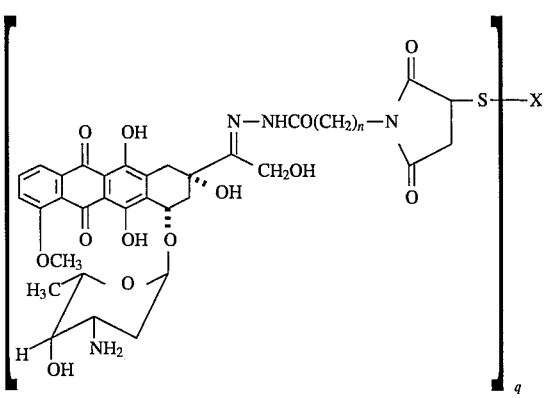

in which n is an integer from 1 to 10;

q is about 1 to about 10; and

X is a ligand reactive with a selected target cell population;

in a pharmacutically acceptable amount associated with a pharmaceutically acceptable carrier, diluent or excipient therefor.

7. A compound of claim 1 in which n is 5.

8. A compound of claim 1 in which X is an immunoglobulin selected from the group consisting of BR96, BR64, L6, a relaxed BR96, a relaxed BR64, a relaxed L6, a chimeric BR96, a chimeric BR64, a chimeric L6, a relaxed chimeric BR96, a relaxed chimeric BR64, a realxed chimeric L6; and, fragments thereof.

9. A compound of claim 8 in which X is a chimeric BR96, a relaxed chimeric BR96; or a fragment thereof.

10. A compound of claim 1 in which X is a ligand selected from the group consisting of bombesin, EGF, transferrin, gastrin, gastrin-releasing peptide, platelet-derived growth factor, IL-2, IL-6, TGF-α, TGF-β, VGF, insulin and insulin-like growth factors I and II.

11. A compound of claim 1 in which X is bombesin.

12. A compound of claim 2 in which Y is O, p is 2, and z is 1.

13. A compound of claim 2 in which Y=$NH_2^+Cl^-$, p is 3, and z is 1.

14. A compound of claim 2 in which z is 0.

15. A compound of claim 2 in which the anthracycline antibiotic moiety is selected from the group consisting of adriamycin, daunomycin, detorubicin, carminomycin, idarubicin, epirubicin, AD-32, 4-morpholinyl-adriamycin and 3'-deamino-3'-(3-cyano-4-morpholinyl)-deoxyrubicin.

16. A compound of claim 12 in which the anthracycline moiety is selected from the group consisting of adriamycin, daunomycin, detorubicin, carminomycin, idarubicin, epirubicin, AD-32, 4-morpholinyl-adriamycin and 3'-deamino-3'-(3-cyano-4-morpholinyl)-deoxyrubicin.

17. A compound of claim 13 in which the anthracycline moiety is selected from the group consisting of adriamycin, daunomycin, detorubicin, carminomycin, idarubicin, epirubicin, AD-32, 4-morpholinyl-adriamycin and 3'-deamino-3'-(3-cyano-4-morpholinyl)-deoxyrubicin.

18. A compound of claim 14 in which the anthracycline moiety is selected from the group consisting of adriamycin, daunomycin, detorubicin, carminomycin, idarubicin, epirubicin, AD-32, 4-morpholinyl-adriamycin and 3'-deamino-3'-(3-cyano-4-morpholinyl)-deoxyrubicin.

19. A compound of claim 15 in which the anthracycline moiety is adriamycin.

20. A compound of claim 16 in which the anthracycline moiety is adriamycin.

21. A compound of claim 17 in which the anthracycline moiety is adriamycin.

22. A compound of claim 18 in which the anthracycline moiety is adriamycin.

23. A compound of claim 19 in which X is an immunoglobulin selected from the group consisting of BR96, BR64, L6, a relaxed BR96, a relaxed BR64, a relaxed L6, a chimeric BR96, a chimeric BR64, a chimeric L6; a relaxed chimeric BR96, a relaxed chimeric BR64, a relaxed chimeric L6; and, fragments thereof.

24. A compound of claim 20 in which X is an immunoglobulin selected from the group consisting of BR96, BR64 and L6, a relaxed BR96, a relaxed BR64, a relaxed L6, a chimeric BR96, a chimeric BR64 and a chimeric L6, a relaxed chimeric BR96, a relaxed chimeric BR64, a relaxed chimeric L6; and, fragments thereof.

25. A compound of claim 21 in which X is an immunoglobulin selected from the group consisting of BR96, BR64 and L6, a relaxed BR96, a relaxed BR64, a relaxed L6, a chimeric BR96, a chimeric BR64, a chimeric L6, a relaxed chimeric BR96, a relaxed chimeric BR64, a relaxed chimeric L6; and, fragments thereof.

26. A compound of claim 22 in which X is an immunoglobulin selected from the group consisting of BR96, BR64 and L6, a relaxed BR96, a relaxed BR64, a relaxed L6, a chimeric BR96, a chimeric BR64, a chimeric L6, a relaxed chimeric BR96, a relaxed chimeric BR64, a relaxed chimeric L6; and, fragments thereof.

27. A compound of claim 23 in which X is a chimeric BR96, a relaxed chimeric BR96; or a fragment thereof.

28. A compound of claim 24 in which X is a chimeric BR96, a relaxed chimeric BR96; or a fragment thereof.

29. A compound of claim 25 in which X is a chimeric BR96, a relaxed chimeric BR96; or a fragment thereof.

30. A compound of claim 26 in which X is a chimeric BR96, a relaxed chimeric BR96; or a fragment thereof.

31. A compound of claim 2 in which X is a ligand selected from the group consisting of bombesin, EGF, transferrin, gastrin, gastrin-releasing peptide, platelet-derived growth factor, IL-2, IL-6, TGF-α, TGF-β, VGF, insulin and insulin-like growth factors I and II.

32. A compound of claim 12 in which X is a ligand selected from the group consisting of bombesin, EGF, transferrin, gastrin, gastrin-releasing peptide, platelet-derived growth factor, IL-2, IL-6, TGF-α, TGF-β, VGF, insulin and insulin-like growth factors I and II.

33. A compound of claim 13 in which X is a ligand selected from the group consisting of bombesin, EGF, transferrin, gastrin, gastrin-releasing peptide, platelet-derived growth factor, IL-2, IL-6, TGF-α, TGF-β, VGF, insulin and insulin-like growth factors I and II.

34. A compound of claim 14 in which X is a ligand selected from the group consisting of bombesin, EGF, transferrin, gastrin, gastrin-releasing peptide, platelet-derived growth factor, IL-2, IL-6, TGF-α, TGF-β, VGF, insulin and insulin-like growth factors I and II.

35. A compound of claim 1 in which X is bombesin.

36. A compound of claim 32 in which X is bombesin.

37. A compound of claim 33 in which X is bombesin.

38. A compound of claim 34 in which X is bombesin.

39. A compound of claim 3 in which X is an immunoglobulin selected from the group consisting of BR96, BR64, L6, a relaxed BR96, a relaxed BR64, a relaxed L6, a chimeric BR96, a chimeric BR64, a chimeric L6, a relaxed chimeric BR96, a relaxed chimeric BR64, a relaxed chimeric L6 ; and, fragments thereof.

40. A compound of claim 3 in which X is a chimeric BR96, a relaxed chimeric BR96, or a fragment thereof.

41. A compound of claim 3 in which X is a protein, or peptide ligand.

42. A compound of claim 41 in which X is selected from the group consisting of bombesin, EGF, transferrin, gastrin, gastrin-releasing peptide.

43. A compound of claim 42 in which X is bombesin.

44. A compound of claim 4 in which X is an immunoglobulin, or a fragment thereof.

45. A compound of claim 4 in which X is an immunoglobulin selected from the group consisting of BR96, BR64, L6, a chimeric BR96, a chimeric BR64, a chimeric L6, a relaxed BR96, a relaxed BR64, a relaxed L6, a relaxed chimeric BR96, a relaxed chimeric BR64, a relaxed chimeric L6; and, fragments thereof.

46. A compound of claim 45 in which X is a chimeric BR96, a relaxed chimeric BR96, or a fragment thereof.

47. A compound of claim 4 in which X is a protein, or peptide ligand.

48. A compound of claim 47 in which X is selected from the group consisting of bombesin, EGF, transferrin, gastrin, gastrin-releasing peptide.

49. A compound of claim 48 in which X is bombesin.

50. A compound of Formula (Id):

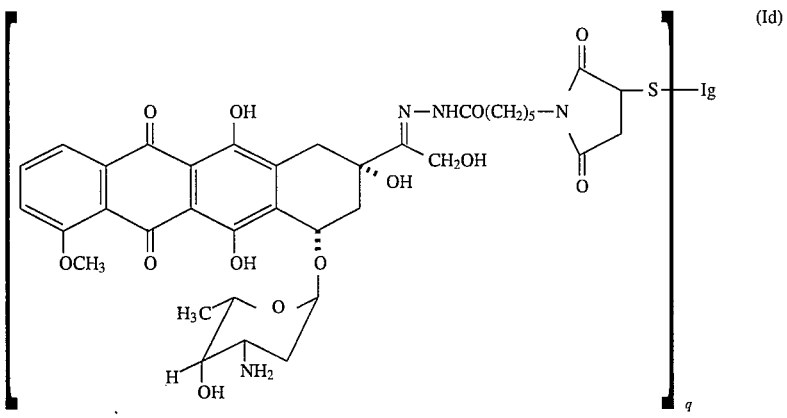

in which q is from about 4 to about 8 and Ig is a relaxed chimeric BR96 antibody, or a fragment thereof.

51. A formulation as claimed in claim 6 in which n is 5, X is a related chimeric BR96 antibody and q is about 4 to about 8.

52. A formulation which comprises as an active ingredient a compound of Formula (Id):

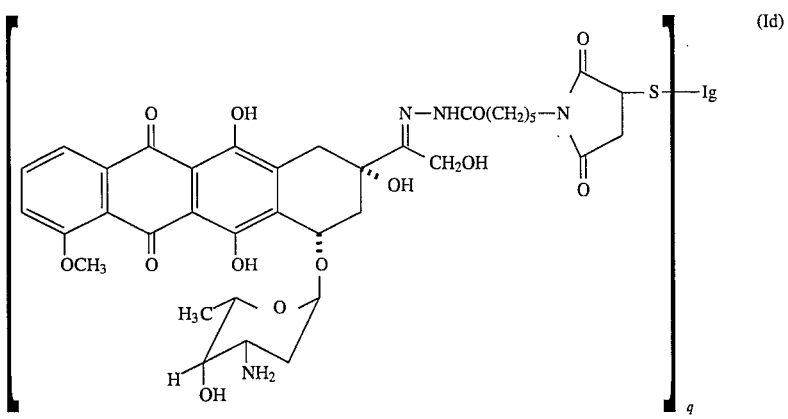

in which q is from about 4 to about 8 and Ig is a relaxed chimeric BR96 antibody, or a fragment thereof, associated with a pharmaceutically acceptable carrier, diluent or excipient therefor.

* * * * *